United States Patent
Robinson et al.

(10) Patent No.: US 8,172,863 B2
(45) Date of Patent: May 8, 2012

(54) METHODS AND APPARATUS FOR CROSSING OCCLUSIONS IN BLOOD VESSELS

(75) Inventors: David Bryan Robinson, Chanhassen, MN (US); Chad John Kugler, Buffalo, MN (US); Matthew Jonathan Olson, Crystal, MN (US); Ross Arlen Olson, Anoka, MN (US); Peter Alan Jacobs, Minneapolis, MN (US)

(73) Assignee: Bridgepoint Medical, Inc., Plymouth, MN (US)

( * ) Notice: Subject to any disclaimer, the term of this patent is extended or adjusted under 35 U.S.C. 154(b) by 345 days.

(21) Appl. No.: 12/453,009

(22) Filed: Apr. 27, 2009

(65) Prior Publication Data
US 2009/0270890 A1 Oct. 29, 2009

Related U.S. Application Data

(60) Provisional application No. 61/048,398, filed on Apr. 28, 2008.

(51) Int. Cl.
*A61B 17/22* (2006.01)

(52) U.S. Cl. ..................................................... 606/159
(58) Field of Classification Search .................. 606/108, 606/127, 128, 159, 182, 191, 192, 193, 194, 606/195, 196, 197, 198, 199, 200; 623/1.11, 623/1.12, 1.23; 81/467, 473, 474, 475, 476, 81/477, 478, 480
See application file for complete search history.

(56) References Cited

U.S. PATENT DOCUMENTS

| 4,020,829 A | | 5/1977 | Wilson et al. |
| 4,233,983 A | | 11/1980 | Rocco |
| 4,262,501 A | * | 4/1981 | Vaughn et al. ................. 464/36 |

(Continued)

FOREIGN PATENT DOCUMENTS
WO WO 0178822 A2 10/2001
(Continued)

OTHER PUBLICATIONS

Colombo, Antonio et al., *Treating Chronic Total Occlusions Using Subintimal Tracking and Reentry: The STAR Technique*, Catheterization and Cardiovascular Interventions, vol. 64:407-411 (2005).

(Continued)

*Primary Examiner* — Ryan Severson
*Assistant Examiner* — Jonathan W Miles
(74) *Attorney, Agent, or Firm* — Finnegan, Henderson, Farabow, Garrett & Dunner, LLP

(57) ABSTRACT

Exemplary embodiments of the present disclosure are directed to a device for facilitating treatment via a vascular wall defining a vascular lumen containing an occlusion therein. The device includes an intravascular device including a shaft having a distal end and a proximal end. The device further includes a handle assembly fixed about the proximal end of the shaft, the handle assembly including a first portion. Further rotation of the first portion in a first direction about a longitudinal axis of the shaft causes rotation of the shaft in the first direction when a torque applied by the first portion to the shaft is below a first maximum torque. Still further, rotation of the first portion in the first direction about a longitudinal axis of the shaft does not cause rotation of the shaft in the first direction when the torque applied by the first portion to the shaft is equal to or above the first maximum torque.

61 Claims, 16 Drawing Sheets

U.S. PATENT DOCUMENTS

| | | | |
|---|---|---|---|
| 4,569,347 A | 2/1986 | Frisbie | |
| 4,581,017 A | 4/1986 | Sahota | |
| 4,621,636 A | 11/1986 | Fogarty | |
| 4,655,103 A * | 4/1987 | Schreiber et al. | 81/474 |
| 4,747,821 A | 5/1988 | Kensey et al. | |
| 4,762,130 A | 8/1988 | Fogarty et al. | |
| 4,774,949 A | 10/1988 | Fogarty | |
| 4,819,634 A | 4/1989 | Shiber | |
| 4,878,495 A | 11/1989 | Grayzel | |
| 4,976,689 A | 12/1990 | Buchbinder et al. | |
| 4,979,939 A | 12/1990 | Shiber | |
| 4,990,134 A | 2/1991 | Auth | |
| 5,071,406 A | 12/1991 | Jang | |
| 5,127,917 A | 7/1992 | Niederhauser et al. | |
| 5,193,546 A | 3/1993 | Shaknovich | |
| 5,201,753 A | 4/1993 | Lampropoulos et al. | |
| 5,263,493 A | 11/1993 | Avitall | |
| 5,275,610 A | 1/1994 | Eberbach | |
| 5,324,263 A | 6/1994 | Kraus et al. | |
| 5,356,418 A | 10/1994 | Shturman | |
| 5,372,587 A | 12/1994 | Hammerslag et al. | |
| 5,383,856 A | 1/1995 | Bersin | |
| 5,385,152 A | 1/1995 | Abele et al. | |
| 5,409,453 A | 4/1995 | Lundquist et al. | |
| 5,415,637 A | 5/1995 | Khosravi | |
| 5,464,395 A | 11/1995 | Faxon et al. | |
| 5,501,667 A | 3/1996 | Verduin, Jr. | |
| 5,505,702 A | 4/1996 | Arney | |
| 5,534,007 A | 7/1996 | St Germain et al. | |
| 5,555,883 A | 9/1996 | Avitall | |
| 5,571,122 A | 11/1996 | Kelly et al. | |
| 5,571,169 A | 11/1996 | Plaia et al. | |
| 5,603,720 A | 2/1997 | Kieturakis | |
| 5,643,298 A | 7/1997 | Nordgren et al. | |
| 5,645,529 A | 7/1997 | Fagan et al. | |
| 5,655,548 A | 8/1997 | Nelson et al. | |
| 5,695,506 A | 12/1997 | Pike et al. | |
| 5,728,133 A | 3/1998 | Kontos | |
| 5,741,270 A | 4/1998 | Hansen et al. | |
| 5,741,429 A | 4/1998 | Donadio, III et al. | |
| 5,779,721 A | 7/1998 | Nash | |
| 5,807,241 A | 9/1998 | Heimberger | |
| 5,810,860 A * | 9/1998 | Adrian | 606/169 |
| 5,824,071 A | 10/1998 | Nelson et al. | |
| 5,830,222 A | 11/1998 | Makower | |
| 5,830,224 A | 11/1998 | Cohn et al. | |
| 5,843,050 A | 12/1998 | Jones et al. | |
| 5,910,133 A | 6/1999 | Gould et al. | |
| 5,916,194 A | 6/1999 | Jacobsen et al. | |
| 5,935,108 A | 8/1999 | Katoh et al. | |
| 5,944,686 A | 8/1999 | Patterson et al. | |
| 5,954,713 A | 9/1999 | Newman et al. | |
| 5,957,900 A | 9/1999 | Ouchi | |
| 5,968,064 A | 10/1999 | Selmon et al. | |
| 5,989,276 A | 11/1999 | Houser et al. | |
| 6,010,449 A | 1/2000 | Selmon et al. | |
| 6,013,055 A | 1/2000 | Bampos et al. | |
| 6,015,405 A | 1/2000 | Schwartz et al. | |
| 6,022,343 A | 2/2000 | Johnson et al. | |
| 6,036,707 A | 3/2000 | Spaulding | |
| 6,036,717 A | 3/2000 | Mers Kelly et al. | |
| 6,059,750 A | 5/2000 | Fogarty et al. | |
| 6,068,638 A | 5/2000 | Makower | |
| 6,071,281 A | 6/2000 | Burnside et al. | |
| 6,071,292 A | 6/2000 | Makower et al. | |
| 6,081,738 A | 6/2000 | Hinohara et al. | |
| 6,099,542 A | 8/2000 | Cohn et al. | |
| 6,117,064 A | 9/2000 | Apple et al. | |
| 6,120,516 A | 9/2000 | Selmon et al. | |
| 6,126,649 A | 10/2000 | VanTassel et al. | |
| 6,155,264 A | 12/2000 | Ressemann et al. | |
| 6,157,852 A | 12/2000 | Selmon et al. | |
| 6,159,225 A | 12/2000 | Makower | |
| 6,183,432 B1 | 2/2001 | Milo | |
| 6,186,972 B1 | 2/2001 | Nelson et al. | |
| 6,190,353 B1 | 2/2001 | Makower et al. | |
| 6,203,559 B1 | 3/2001 | Davis et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 | 5/2001 | Makower | |
| 6,235,000 B1 | 5/2001 | Milo et al. | |
| 6,241,667 B1 | 6/2001 | Vetter et al. | |
| 6,246,914 B1 | 6/2001 | de la Rama et al. | |
| 6,254,588 B1 | 7/2001 | Jones et al. | |
| 6,258,052 B1 | 7/2001 | Milo | |
| 6,266,550 B1 | 7/2001 | Selmon et al. | |
| 6,277,133 B1 | 8/2001 | Kanesaka | |
| 6,283,940 B1 | 9/2001 | Mulholland | |
| 6,283,951 B1 | 9/2001 | Flaherty et al. | |
| 6,283,983 B1 | 9/2001 | Makower et al. | |
| 6,287,317 B1 | 9/2001 | Makower et al. | |
| 6,302,875 B1 | 10/2001 | Makower et al. | |
| 6,330,884 B1 | 12/2001 | Kim | |
| 6,337,142 B2 | 1/2002 | Harder et al. | |
| 6,358,244 B1 | 3/2002 | Newman et al. | |
| 6,375,615 B1 | 4/2002 | Flaherty et al. | |
| 6,379,319 B1 | 4/2002 | Garibotto et al. | |
| 6,387,119 B2 | 5/2002 | Wolf et al. | |
| 6,398,798 B2 | 6/2002 | Selmon et al. | |
| 6,416,523 B1 | 7/2002 | Lafontaine | |
| 6,428,552 B1 | 8/2002 | Sparks | |
| 6,432,127 B1 | 8/2002 | Kim et al. | |
| 6,447,539 B1 | 9/2002 | Nelson et al. | |
| 6,475,226 B1 | 11/2002 | Belef et al. | |
| 6,485,458 B1 | 11/2002 | Takahashi | |
| 6,491,660 B2 | 12/2002 | Guo et al. | |
| 6,491,707 B2 | 12/2002 | Makower et al. | |
| 6,506,178 B1 | 1/2003 | Schubart et al. | |
| 6,508,824 B1 | 1/2003 | Flaherty et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,544,230 B1 | 4/2003 | Flaherty et al. | |
| 6,561,998 B1 | 5/2003 | Roth et al. | |
| 6,565,583 B1 | 5/2003 | Deaton et al. | |
| 6,569,143 B2 | 5/2003 | Alchas et al. | |
| 6,569,145 B1 | 5/2003 | Shmulewitz et al. | |
| 6,569,150 B2 | 5/2003 | Teague et al. | |
| 6,579,311 B1 | 6/2003 | Makower | |
| 6,589,164 B1 | 7/2003 | Flaherty | |
| 6,599,304 B1 | 7/2003 | Selmon et al. | |
| 6,602,241 B2 | 8/2003 | Makower et al. | |
| 6,613,081 B2 | 9/2003 | Kim et al. | |
| 6,616,675 B1 | 9/2003 | Evard et al. | |
| 6,623,448 B2 | 9/2003 | Slater | |
| 6,638,247 B1 | 10/2003 | Selmon et al. | |
| 6,638,293 B1 | 10/2003 | Makower et al. | |
| 6,655,386 B1 | 12/2003 | Makower et al. | |
| 6,656,195 B2 | 12/2003 | Peters et al. | |
| 6,660,024 B1 | 12/2003 | Flaherty et al. | |
| 6,669,709 B1 | 12/2003 | Cohn et al. | |
| 6,685,648 B2 | 2/2004 | Flaherty et al. | |
| 6,685,716 B1 | 2/2004 | Flaherty et al. | |
| 6,694,983 B2 | 2/2004 | Wolf et al. | |
| 6,709,444 B1 | 3/2004 | Makower | |
| 6,719,725 B2 | 4/2004 | Milo et al. | |
| 6,726,677 B1 | 4/2004 | Flaherty et al. | |
| 6,746,426 B1 | 6/2004 | Flaherty et al. | |
| 6,746,462 B1 | 6/2004 | Selmon et al. | |
| 6,746,464 B1 | 6/2004 | Makower | |
| 6,786,884 B1 | 9/2004 | DeCant, Jr. et al. | |
| 6,800,085 B2 | 10/2004 | Selmon et al. | |
| 6,824,550 B1 | 11/2004 | Noriega et al. | |
| 6,830,577 B2 | 12/2004 | Nash et al. | |
| 6,837,868 B1 | 1/2005 | Fajnztajn | |
| 6,860,892 B1 | 3/2005 | Tanaka et al. | |
| 6,863,684 B2 | 3/2005 | Kim et al. | |
| 6,866,676 B2 | 3/2005 | Kieturakis et al. | |
| 6,884,225 B2 | 4/2005 | Kato et al. | |
| 6,905,505 B2 | 6/2005 | Nash et al. | |
| 6,929,009 B2 | 8/2005 | Makower et al. | |
| 6,936,056 B2 | 8/2005 | Nash et al. | |
| 6,942,641 B2 | 9/2005 | Seddon | |
| 6,949,125 B2 | 9/2005 | Robertson | |
| 6,991,617 B2 | 1/2006 | Hektner et al. | |

| | | |
|---|---|---|
| 7,004,173 B2 | 2/2006 | Sparks et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 | 5/2008 | Katoh et al. |
| 7,465,286 B2 | 12/2008 | Patterson et al. |
| 2001/0000041 A1 | 3/2001 | Selmon et al. |
| 2001/0056273 A1 | 12/2001 | C |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0120195 A1 | 6/2003 | Milo et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0171478 A1 | 8/2005 | Selmon et al. |
| 2005/0177105 A1 | 8/2005 | Shalev |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0229646 A1 | 10/2006 | Sparks |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0093783 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0209910 A1 | 8/2009 | Kugler et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| WO | WO 2007/033052 A2 | 3/2007 |
| WO | WO 2008/063621 A2 | 5/2008 |
| WO | WO 2009/054943 A1 | 4/2009 |
| WO | WO 2009/100129 A2 | 8/2009 |
| WO | WO 2009/134346 A2 | 11/2009 |
| WO | WO 2010/019241 A1 | 2/2010 |
| WO | WO 2010/044816 A1 | 4/2010 |

OTHER PUBLICATIONS

International Search Report from PCT/US2009/02571 mailed on Dec. 8, 2009 (6 pages).

International Preliminary Report on Patentability from PCT/US2009/02571 mailed on Nov. 2, 2010 (12 pages).

* cited by examiner

| | FREE TO ROTATE RELATIVE TO SHAFT | FREE TO ROTATE RELATIVE TO HANDLE HOUSING |
|---|---|---|
| PROXIMAL CAP 144 | O | 1 |
| COLLET 146 | O | 1 |
| HANDLE AXLE 140 | O | 1 |
| FIRST CAMMING ELEMENT 156 | O | 1 |
| SECOND CAMMING ELEMENT 158 | 1 | 1 |
| DISTAL CAP 142 | 1 | O |

*FIG. 9*

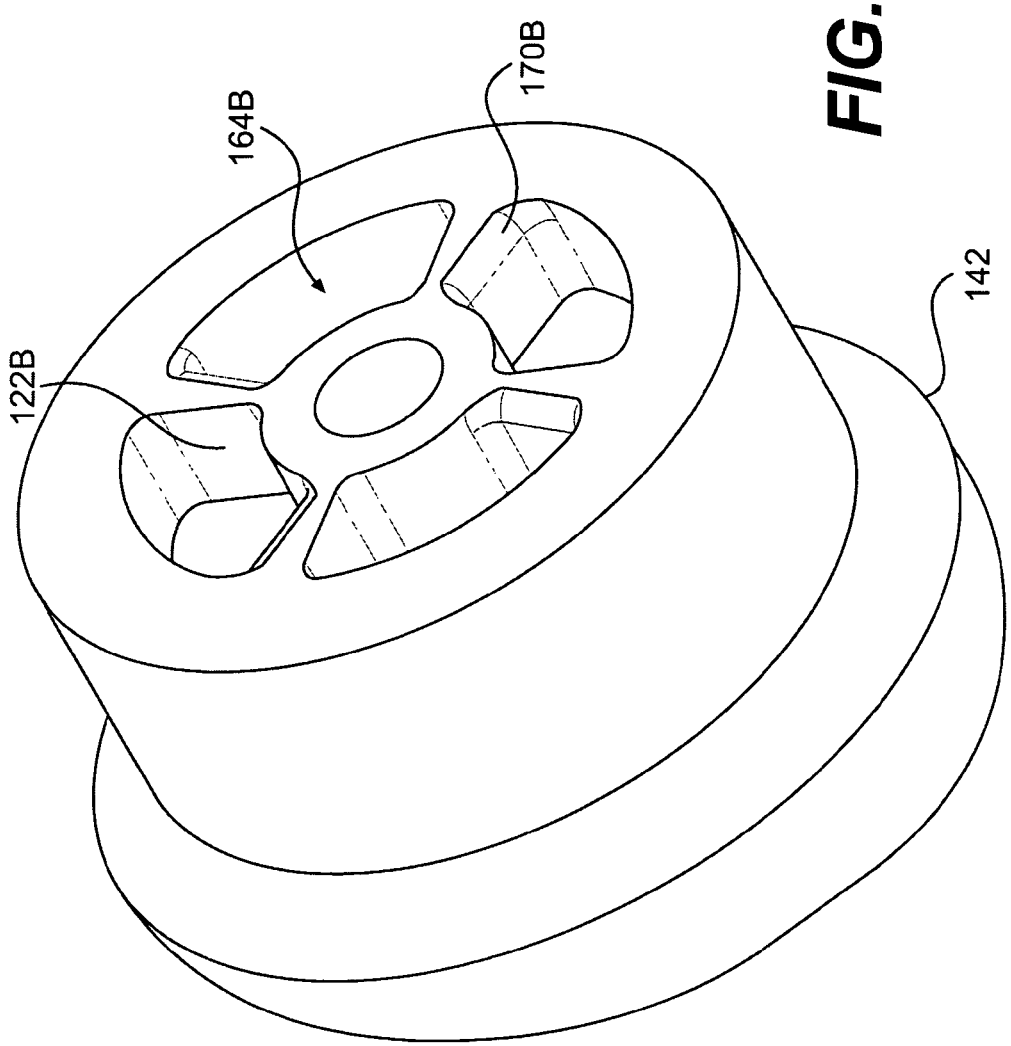

METHODS AND APPARATUS FOR CROSSING OCCLUSIONS IN BLOOD VESSELS

CROSS REFERENCE TO RELATED APPLICATION

This application claims the benefit of U.S. Provisional Application No. 61/048,398, filed Apr. 28, 2008, which is herein incorporated by reference in its entirety.

FIELD OF THE INVENTION

Embodiments of the inventions described herein relate to devices and associated methods for the treatment of chronic total occlusions. More particularly, embodiments of the inventions described herein relate to devices and methods for crossing chronic total occlusions and establishing a pathway blood flow past the chronic total occlusions.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, can not accurately direct endovascular devices toward the visualized lumen, or fail to advance devices through the lesion. Bypass surgery is often the preferred treatment for patients with chronic total occlusions, but less invasive techniques would be preferred.

Described herein are devices and methods employed to exploit the vascular wall of a vascular lumen for the purpose of bypassing a total occlusion of an artery. Exploitation of a vascular wall may involve the passage of an endovascular device into and out of said wall which is commonly and interchangeably described as false lumen access, intramural access, submedial access or in the case of this disclosure, subintimal access.

SUMMARY OF THE INVENTION

In one aspect, the present disclosure is directed to a device for facilitating treatment of a blood vessel. The device includes a shaft having a distal end and a proximal end. The device further includes a handle assembly fixed about the proximal end of the shaft, the handle assembly including a first portion. Further rotation of the first portion in a first direction about a longitudinal axis of the shaft causes rotation of the shaft in the first direction when a torque applied by the first portion to the shaft is below a first maximum torque. Still further, rotation of the first portion in the first direction about the longitudinal axis of the shaft does not cause rotation of the shaft in the first direction when the torque applied by the first portion to the shaft is above the first maximum torque.

In another aspect, the present disclosure is directed to a method of facilitating treatment of a blood vessel. The method may include providing a medical device shaft having a distal end and a proximal end and providing a handle assembly fixed to the proximal end of the shaft. The handle assembly may include a first portion. Further rotation of the first portion in a first direction about a longitudinal axis of the shaft causes rotation of the shaft in the first direction when a torque applied by the first portion to the shaft is below a first maximum torque. Still further rotation of the first portion in the first direction about the longitudinal axis of the shaft does not cause rotation of the shaft in the first direction when the torque applied by the first portion to the shaft is above the first maximum torque. The method may further include rotating the first portion of the handle assembly in a first direction about the longitudinal axis, wherein the rotating applies a torque to the shaft below the first maximum torque, and wherein the rotating causes the shaft to rotate.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrates embodiments of the invention and together with the description, serve to explain the principles of the invention.

BRIEF DESCRIPTION OF THE DRAWINGS

In FIG. 2, a total occlusion is shown blocking one of the coronary arteries of the heart. The presence of the occlusion in the coronary artery may result in inadequate oxygenation of cardiac muscle located distal of the occlusion.

FIG. 4 is a plan view showing an assembly including the crossing device shown in the previous figure. In the embodiment of FIG. 4, a handle assembly is coupled to the crossing device. A physician may use the handle assembly to rotate the crossing device. Rotation of crossing device can be achieved, for example, by rolling the handle assembly between the thumb and forefinger of two hands as shown in FIG. 4.

FIG. 9 includes a table describing the relative freedom of rotation between the handle assembly elements shown in the previous figure and the shaft. This table also describes the relative freedom of rotation between various handle assembly elements and the handle housing.

FIG. 16 is an enlarged isometric view showing a distal cap. The distal cap defines a plurality of recesses. Each recess is dimensioned to receive a ramped surface of the second camming element shown in the previous figure.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

The following detailed description should be read with reference to the drawings in which similar elements in different drawings are numbered the same. The drawings, which are not necessarily to scale, depict illustrative embodiments and are not intended to limit the scope of the invention.

Figure 1:
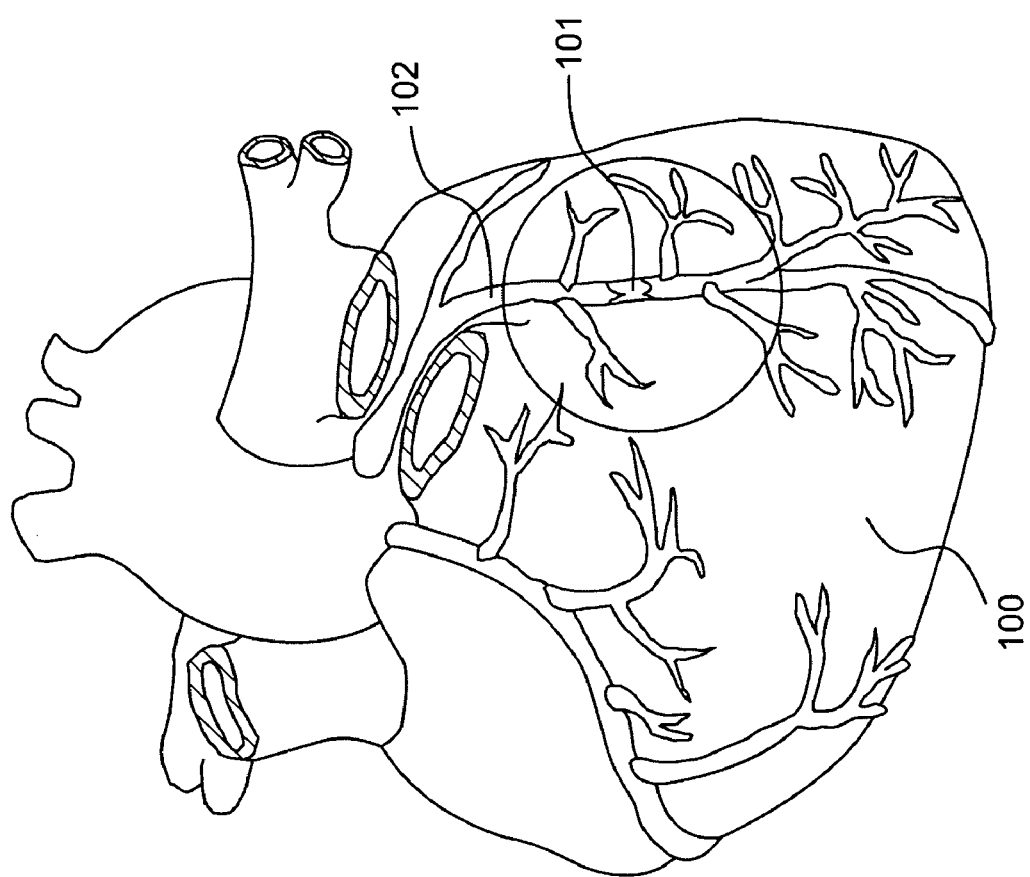
FIG. 1 is a schematic representation of a human heart. The heart includes a plurality of coronary arteries that are all susceptible to occlusion. Occlusions can significantly reduce blood flow to distal portions of the coronary arteries. Under certain physiological circumstances and given sufficient time, some occlusions may become total or complete occlusions.

FIG. 1 is a schematic representation of a human heart 100. Heart 100 includes a plurality of coronary arteries 102, all of which are susceptible to occlusion. Under certain physiological circumstances and given sufficient time, some occlusions may become total or complete, such as total occlusion 101. As used herein, the terms total occlusion and complete occlusion are intended to refer to the same or similar degree of occlusion with some possible variation in the age of the occlusion. Generally, a total occlusion refers to a vascular lumen that is ninety percent or more functionally occluded in cross-sectional area, rendering it with little to no blood flow therethrough and making it difficult or impossible to pass a conventional guide wire therethrough. Also generally, the older the total occlusion the more organized the occlusive material will be and the more fibrous and calcified it will become. According to one accepted clinical definition, a total occlusion is considered chronic if it is greater than two weeks old from symptom onset.

Figure 2:
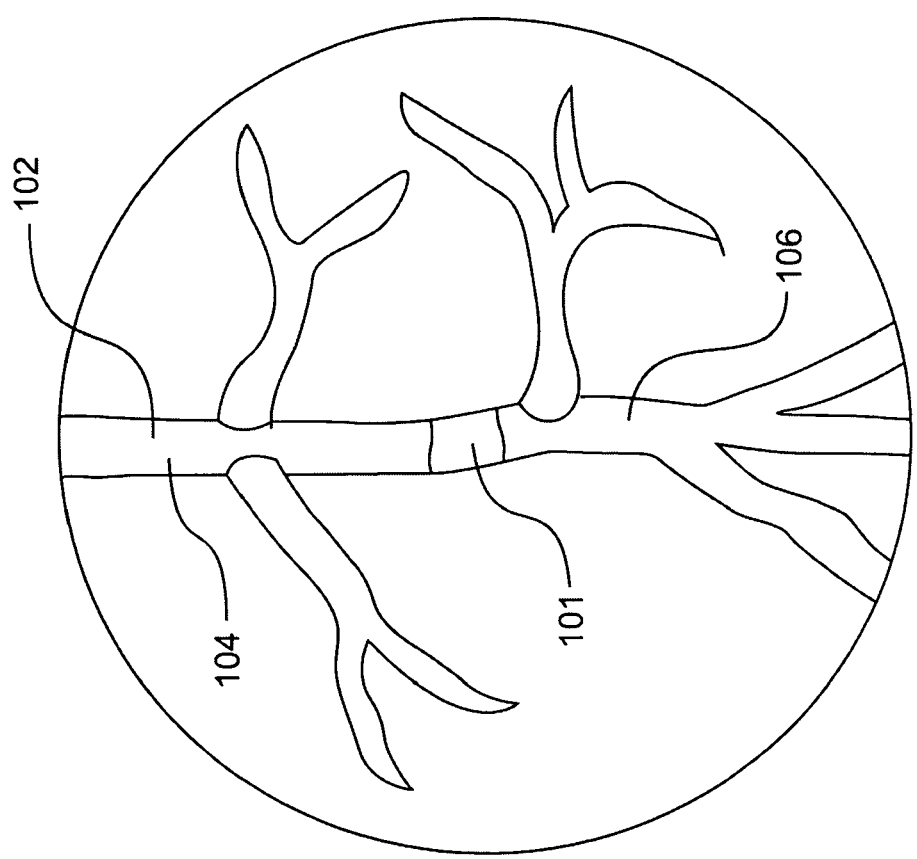
FIG. 2 is an enlarged view further illustrating a portion of the heart shown in the previous figure.

FIG. 2 is an enlarged view further illustrating a portion of heart 100 shown in the previous figure. In FIG. 2, a total occlusion 101 is shown within a coronary artery 102. Generally, a proximal segment 104 of artery 102 (i.e., the portion of artery 102 proximal of total occlusion 101) may be easily accessed using endovascular devices and has adequate blood flow to supply the surrounding cardiac muscle. A distal segment 106 of artery 102 (i.e., the portion of artery 102 distal of total occlusion 101) is not easily accessed with interventional devices and has significantly reduced blood flow as compared to proximal segment 104.

Figure 3:
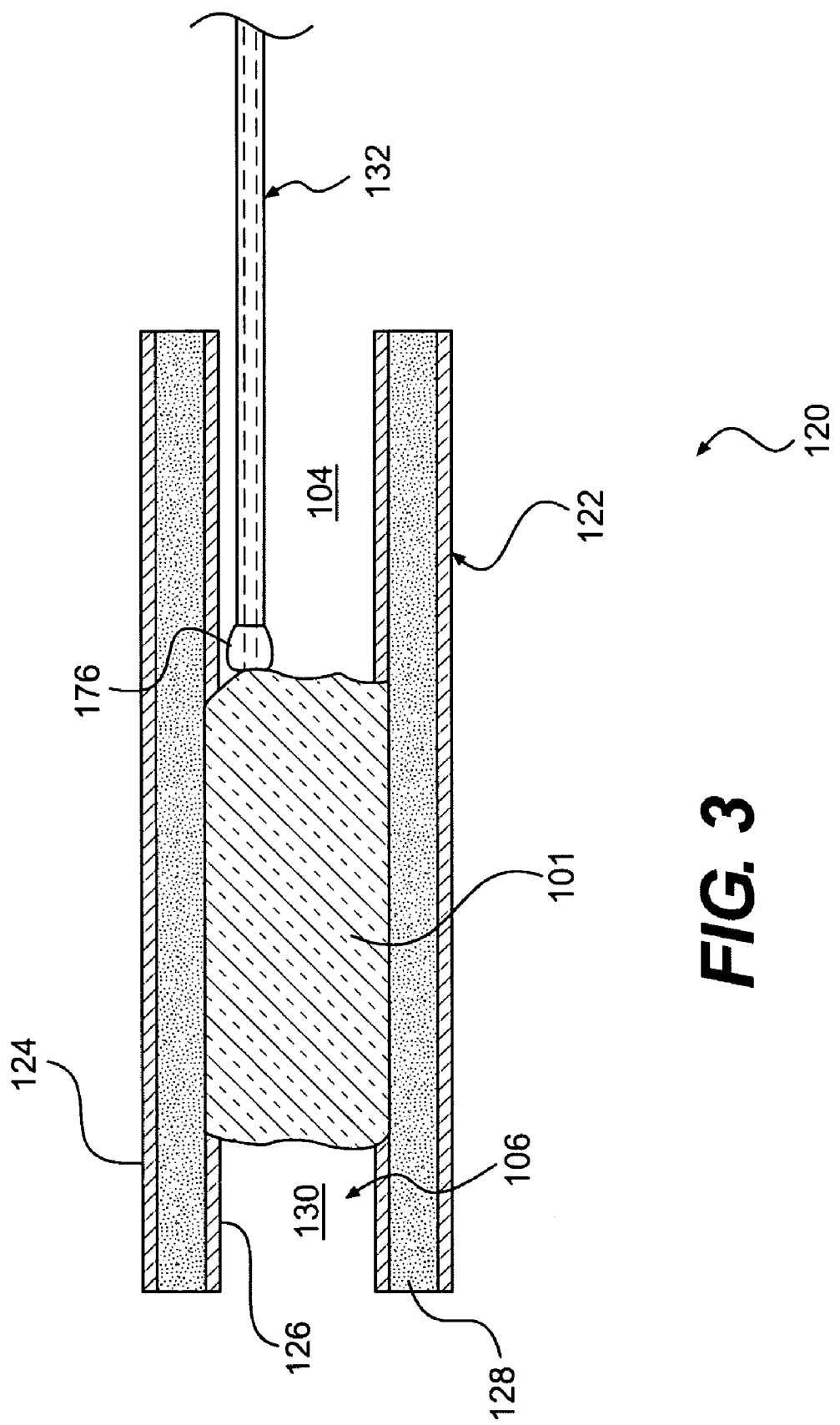
FIG. 3 is a cross-sectional view of an artery having a wall. The wall of the artery is shown having three layers. The outermost layer of wall is the adventitia and the innermost layer of wall is the intima. The tissues extending between intima and adventitia may be collectively referred to as the media.

FIG. 3 is a cross-sectional view of a blood vessel 120 having a wall 122. In FIG. 3, wall 122 of blood vessel 120 is shown having three layers. The outermost layer of wall 122 is an adventitia 124 and the innermost layer of wall 122 is an intima 126. The tissues extending between intima 126 and adventitia 124 may be collectively referred to as a media 128. For purposes of illustration, intima 126, media 128 and adventitia 124 are each shown as a single homogenous layer in FIG. 3. In the human body, however, the intima and the media each comprise a number of sub-layers. The transition between the external-most portion of the intima and the internal-most portion of the media is sometimes referred to as the subintimal space. Intima 126 defines a true lumen 130 of blood vessel 120. In FIG. 3, occlusion 101 is shown blocking true lumen 130. Occlusion 101 divides true lumen 130 into proximal segment 104 and distal segment 106. In FIG. 3, a distal portion of a crossing device 132 is shown extending into proximal segment 104 of true lumen 130.

As shown in FIG. 3, methods described in this document may include the step of advancing a crossing device to a location proximate an occlusion in a blood vessel. The exemplary methods described in this document may also include the step of advancing crossing device 132 between occlusion 101 and adventitia 124. In some useful methods, crossing device 132 may be rotated as the distal end of crossing device 132 is advanced between occlusion 101 and adventitia 124. Rotating crossing device 132 assures that the coefficient of friction at the interface between the crossing device and the surrounding tissue will be a kinetic coefficient of friction rather than a static coefficient of friction.

Figure 4:
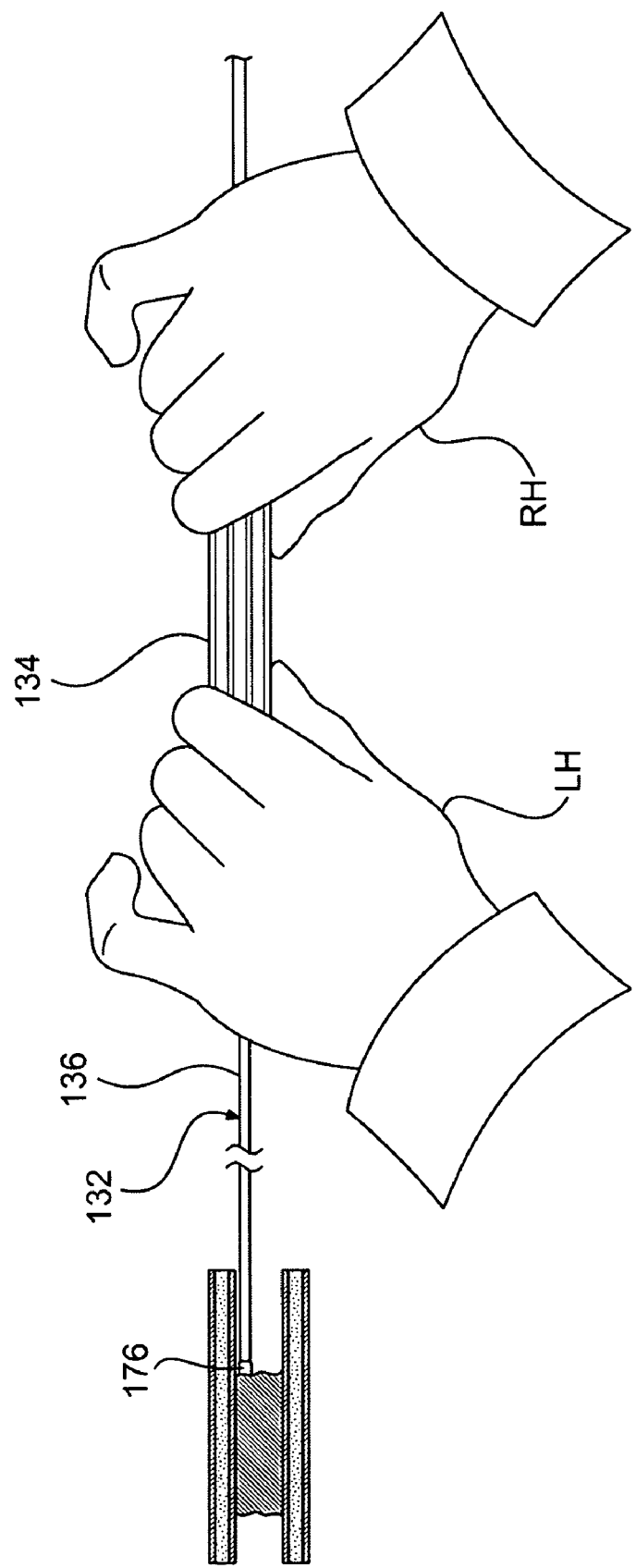
In FIG. 4, an occlusion is blocking the true lumen of the artery. The distal tip of a crossing device has been positioned in the true lumen of the artery near the occlusion. Methods described in this document may include the step of advancing the distal end of the crossing device to a location distal of the occlusion in the coronary artery. These methods may also include the step of advancing the crossing device between the occlusion and the adventitia of the artery.

FIG. 4 is a plan view showing an assembly including crossing device 132 shown in the previous figure. In the embodiment of FIG. 4, a handle assembly 134 is coupled to crossing device 132. In FIG. 4, handle assembly 134 is shown disposed about a proximal portion of a shaft 136 of crossing device 132. In FIG. 4, a portion of handle assembly 134 is positioned between the thumb and forefinger of a left hand LH. A second portion of handle assembly 134 is disposed between the thumb and forefinger of a right hand RH. The fingers of left hand LH and right hand RH are shown wrapping in a clockwise direction loosely around shaft 136 in FIG. 4. The thumb of left hand LH is shown pointing in a generally proximal direction in FIG. 4. The thumb of right hand RH is shown pointing in a generally distal direction in FIG. 4. For the purposes of this disclosure, clockwise and counter clockwise are viewed from the perspective of a viewer positioned near the proximal end of shaft 136 viewing an imaginary clock located near distal tip 176. With reference to FIG. 4, it will be appreciated that handle assembly 134 is long enough to receive the thumb and forefingers of a physician's right and left hands. When this is the case, a physician can use two hands to rotate handle assembly 134.

Rotation of crossing device 132 can be achieved by rolling handle assembly 134 between the thumb and forefinger of one hand. Two hands may also be used to rotate handle assembly 134 as shown in FIG. 4. In some useful methods, crossing device 132 can be rotated and axially advanced simultaneously. Rotating crossing device 132 assures that the coefficient of friction at the interface between the crossing device and the surrounding tissue will be a kinetic coefficient of friction and not a static coefficient of friction.

In some useful methods in accordance with the present disclosure, crossing device 132 is rotated at a rotational speed of between about 2 revolutions per minute and about 200 revolutions per minute. In some particularly useful methods in accordance with the present disclosure, crossing device 132 is rotated at a rotational speed of between about 50 revolutions per minute and about 150 revolutions per minute. Crossing device 132 may be rotated by hand as depicted in FIG. 4. It is also contemplated that a mechanical device (e.g., an electric motor) may be used to rotate crossing device 132.

Figure 5:
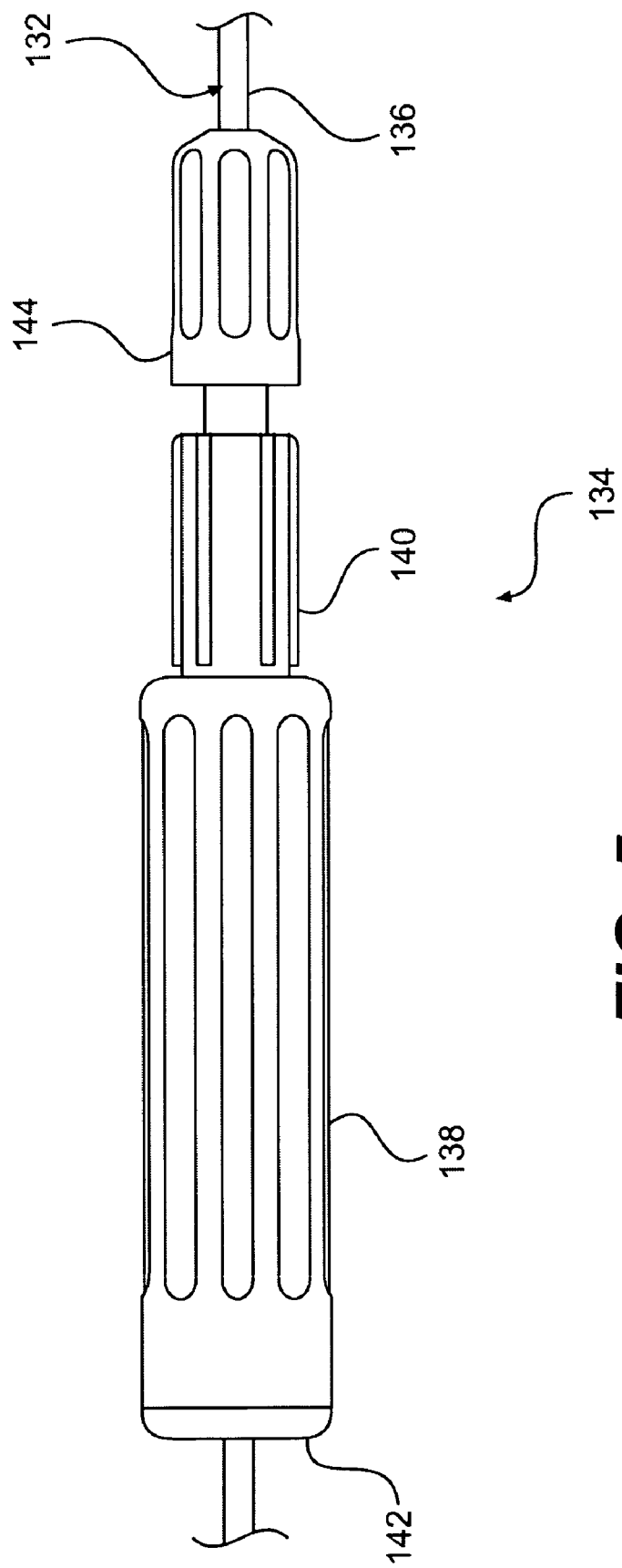
FIG. 5 is an enlarged plan view showing the handle assembly shown in the previous figure. The handle assembly comprises a handle housing disposed about a handle axle. In the embodiment of FIG. 5, the handle axle is fixed to a shaft of the crossing device.

FIG. 5 is an enlarged plan view showing handle assembly 134 shown in the previous figure. Handle assembly 134 comprises a handle housing 138. A distal cap 142 is fixed (e.g., with a threaded connection) to the distal end of handle housing 138. A handle axle 140 is partially disposed in handle housing 138. In the embodiment of FIG. 5, handle axle 140 is selectively fixed to shaft 136 of crossing device 132. A proximal cap 144 is fixed (e.g., with a threaded connection) to the proximal end of handle axle 140.

Figure 6:
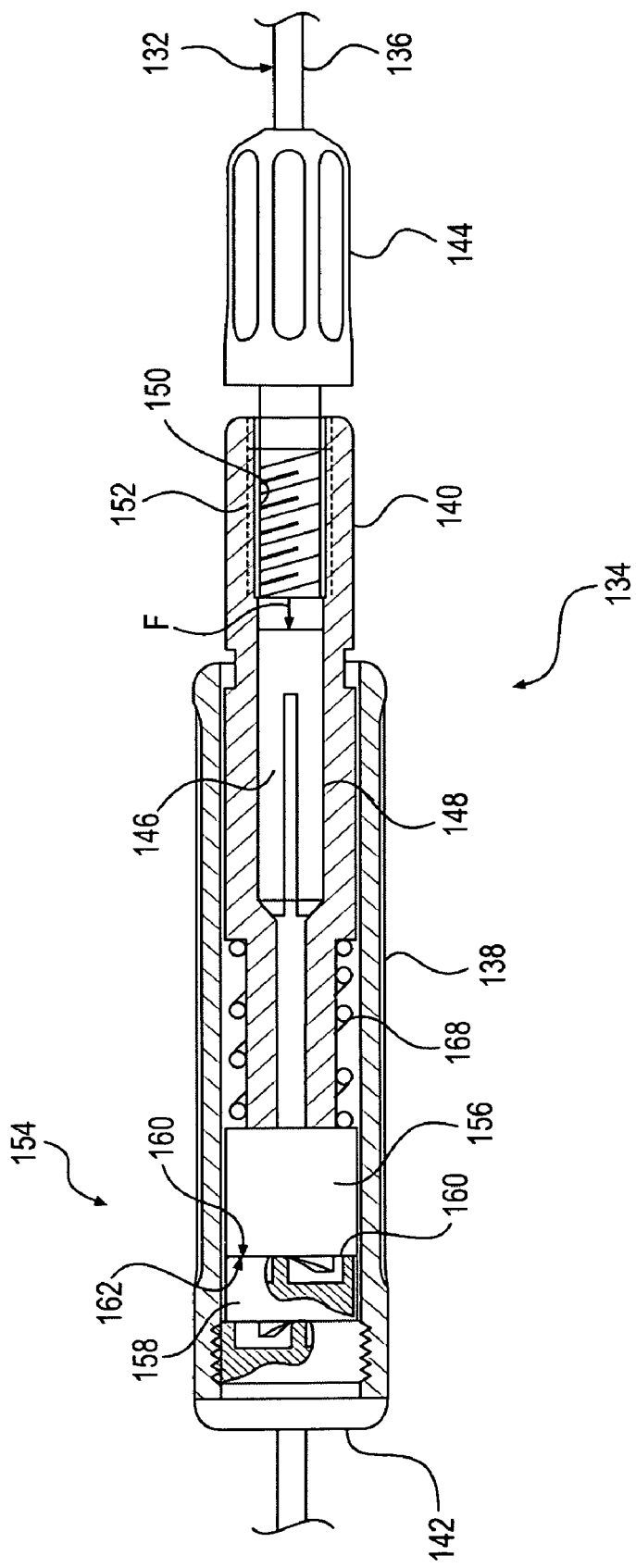
FIG. 6 is a partial cross-sectional view of the handle assembly shown in the previous figure. The handle assembly includes a handle housing, a handle axle, a proximal cap, and a collet. In the embodiment of FIG. 6, the proximal cap, the collet, and the handle axle cooperate to pinch the shaft between the jaws of the collet. Under normal operating conditions, the handle axle will be fixed to the shaft when the shaft is pinched between the jaws of the collet.

FIG. 6 is a partial cross-sectional view of handle assembly 134 shown in the previous figure. With reference to FIG. 6 it will be appreciated that shaft 136 of crossing device 132 extends through handle assembly 134. Handle assembly 134 includes handle housing 138, handle axle 140, proximal cap 144, and a collet 146. In the embodiment of FIG. 6, proximal cap 144, collet 146, and handle axle 140 cooperate to pinch shaft 136 between the jaws of collet 146. Under normal operation, handle axle 140 will be selectively fixed to shaft 136 when shaft 136 is pinched between the jaws of collet 146.

As shown in FIG. 6, collet 146 of handle assembly 134 is disposed in a cavity 148 defined by handle axle 140. Handle axle 140 includes female threads 152 that are dimensioned to receive male threads 150 of proximal cap 144. In FIG. 6, proximal cap 144 is shown threadingly engaging a proximal portion of handle axle 140. When handle axle 140 and proximal cap 144 comprise right handed threads, a distally directed force F can be applied to collet 146 by rotating proximal cap 144 in a clockwise direction. Applying a distally directed force to collet 146 causes the jaws of collet 146 to pinch shaft 136. Collet 146 and handle axle 140 both include tapered surfaces that cause collet 146 to pinch shaft 136 when collet 146 is urged in a distal direction relative to handle axle 140.

Handle assembly 134 of FIG. 6 comprises a torque control mechanism 154. Torque control mechanism 154 includes a first camming element 156 that is coupled to a distal portion of handle axle 140. In some useful embodiments, the distal portion of handle axle 140 includes a plurality of splines 184 (see FIGS. 11 and 13) and first camming element 156 includes grooves that are dimensioned to receive the splines of the handle axle 140. A distal surface 160 of first camming element 156 contacts a proximal end 162 of a second camming element 158. In the embodiment of FIG. 6, a spring 168 urges first camming element 156 against second camming element 158. Spring 168 also urges second camming element 158 against distal cap 142.

Figure 7:
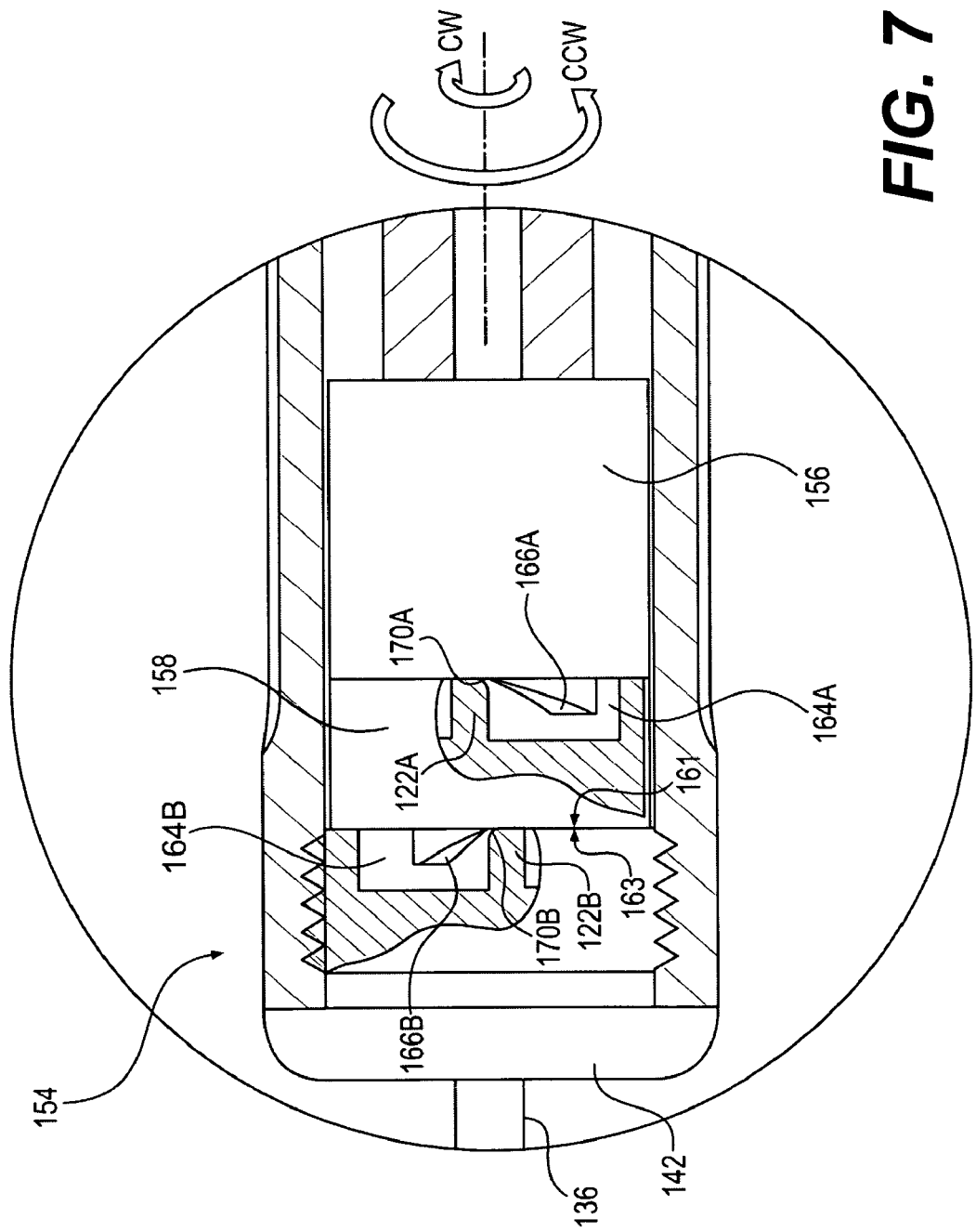
FIG. 7 is an enlarged cross-sectional view showing a portion of the assembly shown in the previous figure. In particular, FIG. 7 provides an enlarged cross-sectional view of the first camming element and the second camming element. In the embodiment of FIG. 7, the first camming element and the second camming element form part of a torque control mechanism. In some useful embodiments, the first camming element and the second camming element are dimensioned so that the torque control mechanism will provide a first maximum torque when the shaft is being rotated in a clockwise direction and a second maximum torque when the shaft is being rotated in a counter-clockwise direction. In some particularly useful embodiments, the second maximum torque is different from the first maximum torque.

FIG. 7 is an enlarged partial cross-sectional view showing a portion of the assembly shown in the previous figure. First camming element 156 and second camming element 158 are visible in FIG. 7. Second camming element 158 defines a plurality of recesses 164A. Each recess 164A is dimensioned to receive a ramped surface 166A of first camming element 156. Each recess 164A is partially defined by a wall 122A. Each wall 122A includes a ramp engaging surface 170A. In the embodiment of FIG. 7, each ramp engaging surface 170A has a radius.

The distal surface 161 of second camming element 158 contacts a proximal end 163 of distal cap 142. Distal cap 142 defines a plurality of recesses 164B. Each recess 164B is dimensioned to receive a ramped surface 166B of second camming element 158. Each recess 164B is partially defined by a wall 122B. Each wall 122B includes a ramp engaging surface 170B. In the embodiment of FIG. 7, each ramp engaging surface 170B has a radius.

In the embodiment of FIG. 7, first camming element 156 and second camming element 158 form part of a torque control mechanism 154. If a predetermined maximum torque is applied to shaft 136 in a clockwise direction CW, then the ramp engaging surface 170A of second camming element 158 will ride up ramped surfaces 166A of first camming element 156. If a predetermined maximum torque is applied to shaft 136 in a counter-clockwise direction CCW, then the ramp engaging surface 170B of distal cap 142 will ride up ramped surfaces 166B of second camming element 156.

In some useful embodiments, first camming element 156 and second camming element 158 are dimensioned so that torque control mechanism 154 will provide a first maximum torque when shaft 136 is being rotated in a clockwise direction and a second maximum torque when shaft 136 is being rotated in a counter-clockwise direction. In some useful embodiments, the second maximum torque is different from the first maximum torque. Also in some useful embodiments, the difference between the second maximum torque and the first maximum torque corresponds to a difference in strength of shaft 136 when subjected to a counterclockwise torque versus a clockwise torque.

Figure 8:
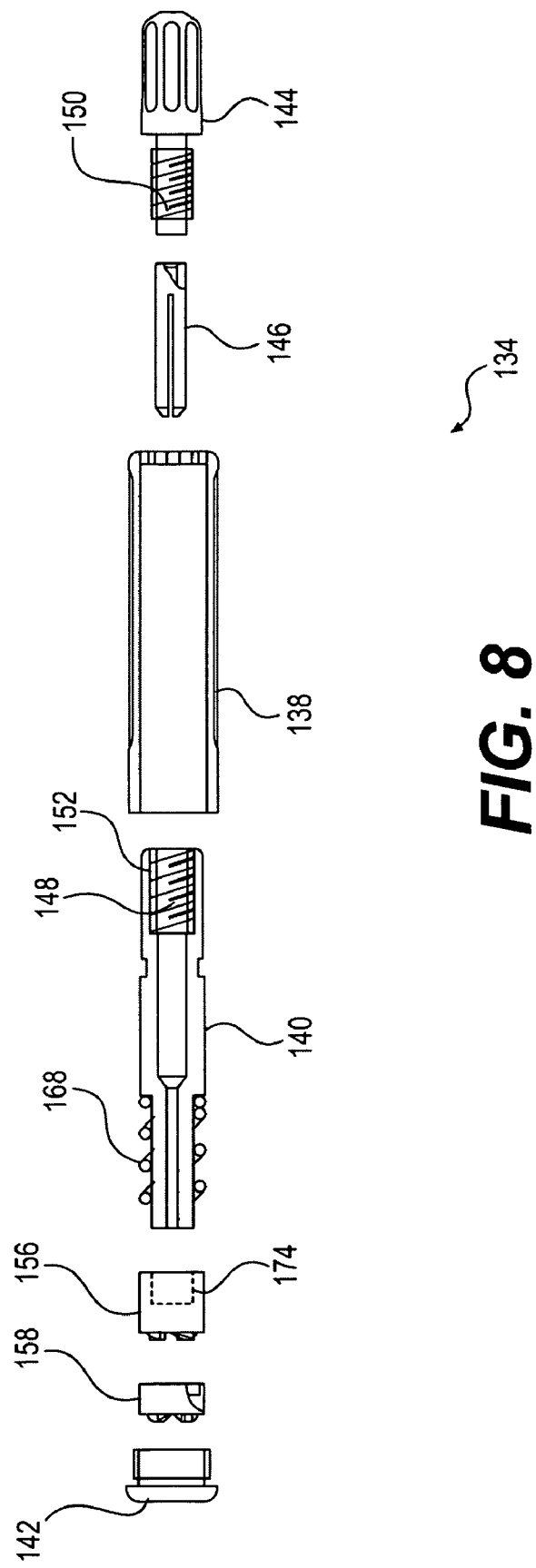
FIG. 8 is an exploded plan view showing several components of an exemplary handle assembly in accordance with the present disclosure.

FIG. 8 is an exploded plan view showing several components of handle assembly 134. Handle assembly 134 comprises handle housing 138 and handle axle 140. Handle axle 140 may be inserted into handle housing 138 so that handle housing 138 is disposed about a portion of handle axle 140. Collet 146 may be inserted into cavity 148 defined by handle axle 140. Handle axle 140 includes female threads 152 that are dimensioned to receive male threads 150 of proximal cap 144. Proximal cap 144 may be advanced into cavity 148 defined by handle axle 140.

A first camming element 156 defines a socket 174 that is dimensioned to receive the distal portion of handle axle 140. In some useful embodiments, the distal portion of handle axle 140 includes a plurality of splines 184 and first camming element 156 includes grooves that are dimensioned to receive splines 184 of the handle axle 140. Handle assembly 134 also includes a second camming element 158 and distal cap 142.

FIG. 9 includes a table describing relative freedom of movement between various elements shown in FIG. 8. The left-most column of this table lists each of the elements shown in the previous figure. The top row in this table lists two statements. First, the element is free to rotate relative to the shaft. Second, the element is free to rotate relative to the handle housing. The table also includes boolean logic values of O and 1. A boolean logic value of 1 indicates that the statement is true for a given element. A boolean logic value of O indicates that the statement is false for a given element.

As described above, proximal cap 144, collet 146, and handle axle 140 cooperate to pinch the shaft between the jaws of collet 146. Accordingly, proximal cap 144, collet 146, and handle axle 140 are not free to rotate relative to the shaft under normal operating conditions. In the embodiment of FIG. 9, first camming element 156 and handle axle 140 engage one another at a splined connection. Accordingly, first camming element 156 and handle axle 140 are not free to rotate relative to one another. In the embodiment of FIG. 9, distal cap 142 and handle housing 138 engage one another at a threaded connection. Once this thread is tightened, distal cap 142 is not free to rotate relative to handle housing under normal operation.

Figure 10:
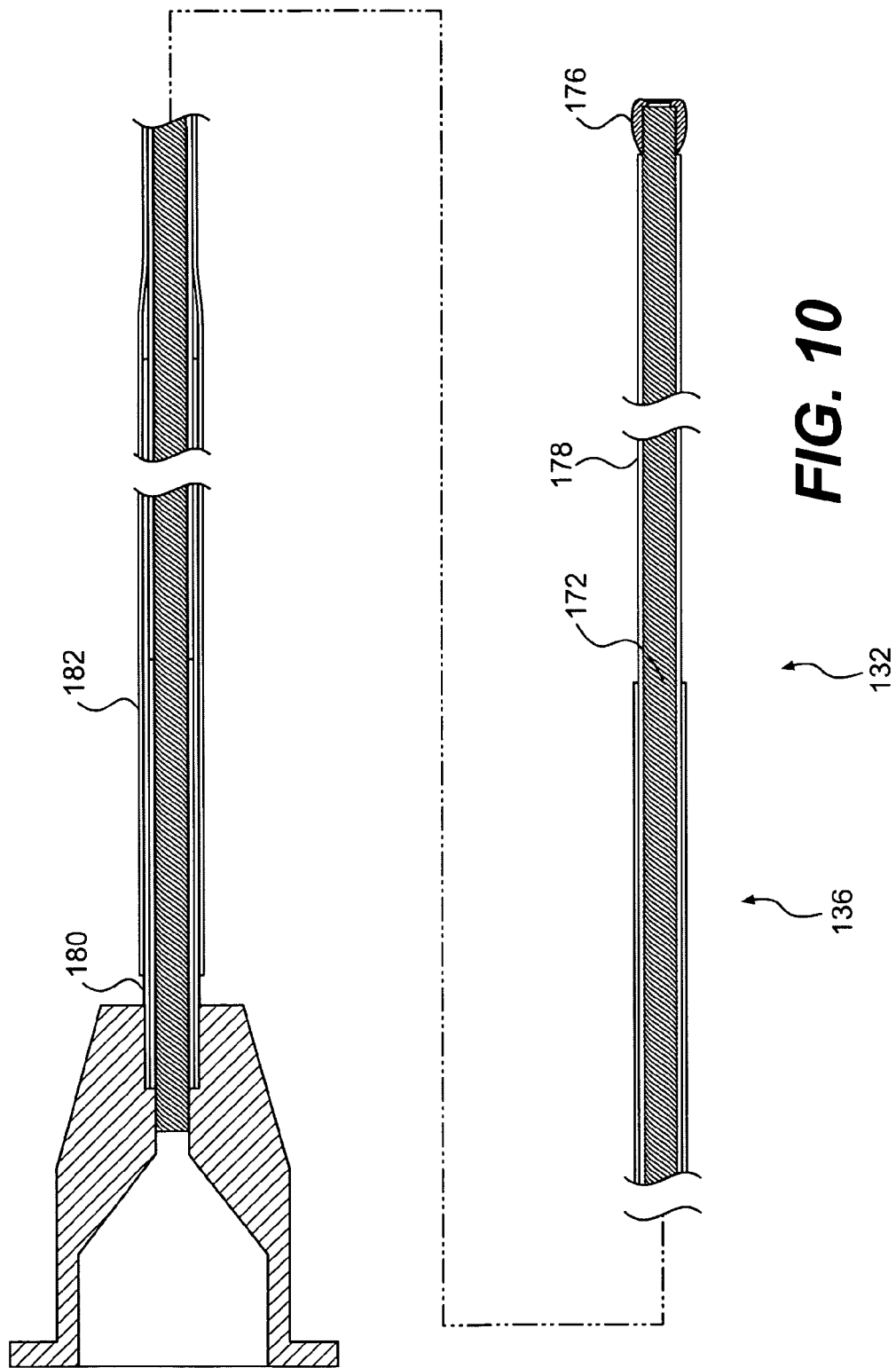
FIG. 10 is a partial cross-sectional view of an exemplary crossing device. The crossing device comprises a tip that is fixed to a distal end of a shaft. In the exemplary embodiment of FIG. 10, the shaft includes a coil comprising a plurality of filars that are wound in a generally helical shape.

FIG. 10 is a partial cross-sectional view of an exemplary crossing device 132. Crossing device 132 of FIG. 10 comprises a tip 176 that is fixed to a distal end of a shaft 136. In the exemplary embodiment of FIG. 10, shaft 136 comprises a coil 172, a sleeve 178, a tubular body 180, and a sheath 182.

Tip 176 is fixed to a distal portion of coil 172. Coil 172 comprises a plurality of filars that are each wound in a generally helical shape. In the embodiment of FIG. 10, coil 172 comprises a left-hand wound coil. Embodiments are also possible in which coil 172 comprises a right-hand wound coil. In some useful embodiments of crossing device 132, coil 172 comprises eight, nine or ten filars wound into the shape illustrated in FIG. 10. Crossing device 132 includes sleeve 178 that is disposed about a portion of coil 172. Sleeve 178 may comprise, for example, PET shrink tubing, i.e. polyethylene terephthalate.

Sleeve 178 and coil 172 both extend into a lumen defined by a tubular body 180. Tubular body 180 may comprise, for example hypodermic tubing formed of Nitnol (i.e. nickel titanium alloy). With reference to FIG. 10, it will be appreciated that a proximal portion of sleeve 178 is disposed between tubular body 180 and coil 172. In some embodiments of crossing device 132, a distal portion of tubular body 180 defines a helical cut. This helical cut may be formed, for example, using a laser cutting process. The helical cut may be shaped and dimensioned to provide an advantageous transition in lateral stiffness proximate the distal end of tubular body 180.

A proximal portion of coil 172 extends proximally beyond the distal end of tubular body 180. A hub is fixed to a proximal portion of coil 172 and a proximal portion of tubular body 180. The hub may comprise, for example, a luer fitting. A sheath 182 is disposed about a portion of tubular body 180 and a portion of sleeve 178. In some embodiments of crossing device 132, sheath 182 comprises HYTREL, a thermoplastic elastomer.

With reference to FIG. 10, it will be appreciated that tubular body 180, coil 172, sleeve 178, and sheath 182 each have a proximal end and a distal end. The proximal end of sheath 182 is disposed between the proximal end of tubular body 180 and the proximal end of sleeve 178. The distal end of sleeve 178 is positioned proximate tip 176 that is fixed to the distal end of coil 172. The distal end of sheath 182 is located between the distal end of tubular body 180 and the distal end of sleeve 178. With reference to FIG. 10, it will be appreciated that sheath 182 overlays the distal end of tubular body 180.

With reference to FIG. 10, it will be appreciated that tip 176 has a generally rounded shape. The generally rounded shape of tip 176 may reduce the likelihood that crossing device 132 will penetrate the adventitia of an artery. Tip 176 may be formed from a suitable metallic material including but not limited to stainless steel, silver solder, and braze. Tip 176 may also be formed from suitable polymeric materials or adhesives including but not limited to polycarbonate, polyethylene and epoxy. In some embodiments of crossing device 132, the outer surface of tip 176 comprises a generally non-abrasive surface. For example, the outer surface of tip 176 may have a surface roughness of about 25 micrometers or less. A tip member having a relatively smooth outer surface may reduce the likelihood that the tip member will abrade the adventitia of an artery.

Figure 11:
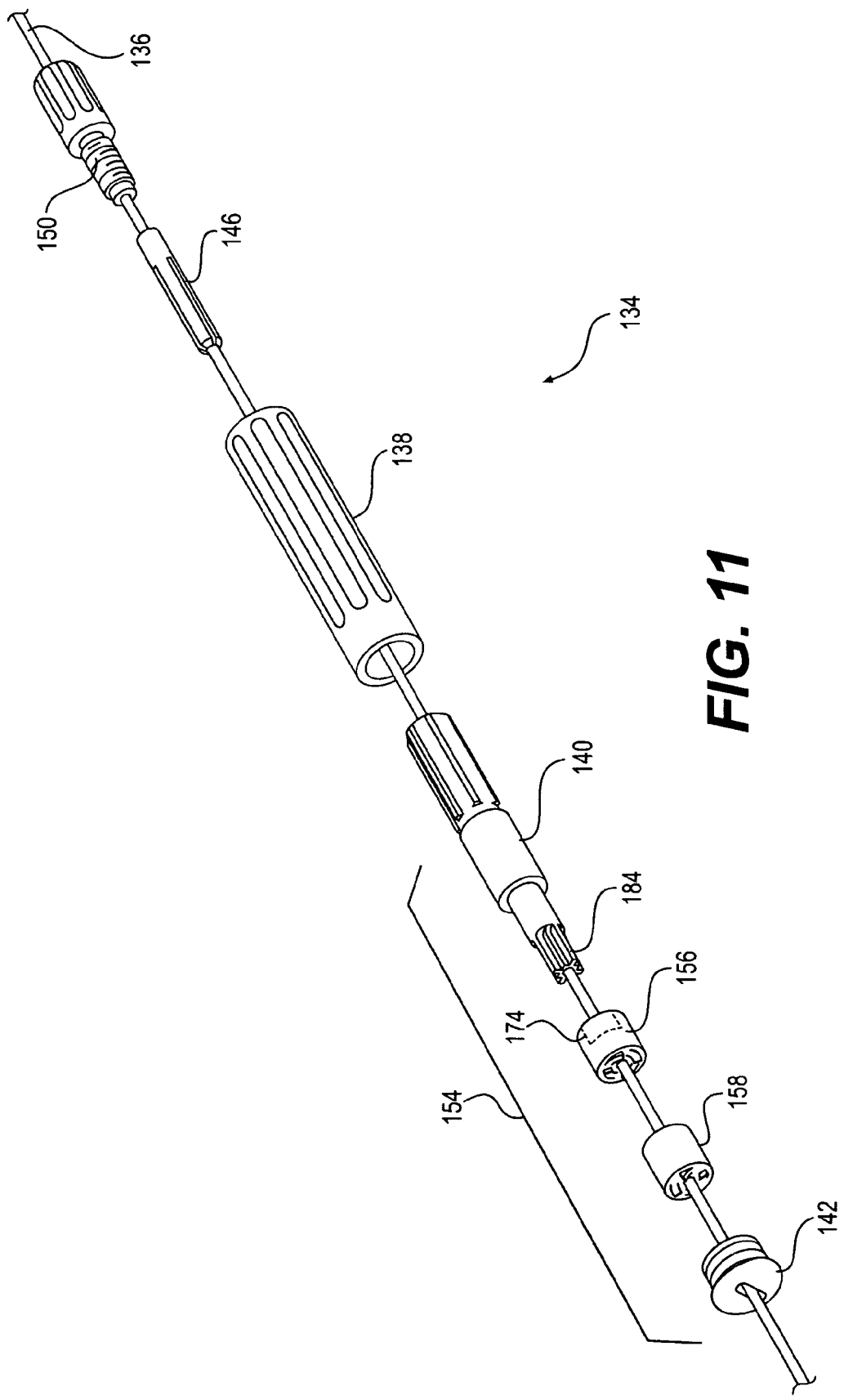
FIG. 11 is an exploded isometric view showing several components of a handle assembly that is disposed about the shaft shown in the previous figure.

FIG. 11 is an exploded isometric view showing several components of handle assembly 134 that is disposed about shaft 136 shown in the previous figure. Handle assembly 134 of FIG. 11 comprises torque control mechanism 154. Torque control mechanism 154 includes first camming element 156 and second camming element 158. First camming element 156 and second camming element 158 are dimensioned so that torque control mechanism 154 will provide a first maximum torque when shaft 136 is being rotated in a clockwise direction and a second maximum torque when shaft 136 is being rotated in a counter-clockwise direction. In some useful embodiments, the second maximum torque is different from the first maximum torque. Also in some useful embodiments, the difference between the second maximum torque and the first maximum torque corresponds to a difference in strength of shaft 136 when subjected to a counterclockwise torque versus a clockwise torque.

Handle assembly 134 comprises handle housing 138 and handle axle 140. Handle axle 140 may be inserted into handle housing 138 so that handle housing 138 is disposed about a portion of handle axle 140. Collet 146 may be inserted into a cavity defined by handle axle 140. Handle axle 140 includes female threads that are dimensioned to receive male threads 150 of proximal cap 144. Proximal cap 144 may be advanced into cavity 148 defined by handle axle 140.

First camming element 156 defines socket 174 that is dimensioned to receive a distal portion of handle axle 140. In some useful embodiments, the distal portion of handle axle 140 includes a plurality of splines 184 and first camming element 156 includes grooves that are dimensioned to receive the splines of the handle axle 140. Handle assembly 134 also includes second camming element 158 and distal cap 142.

Figure 12:
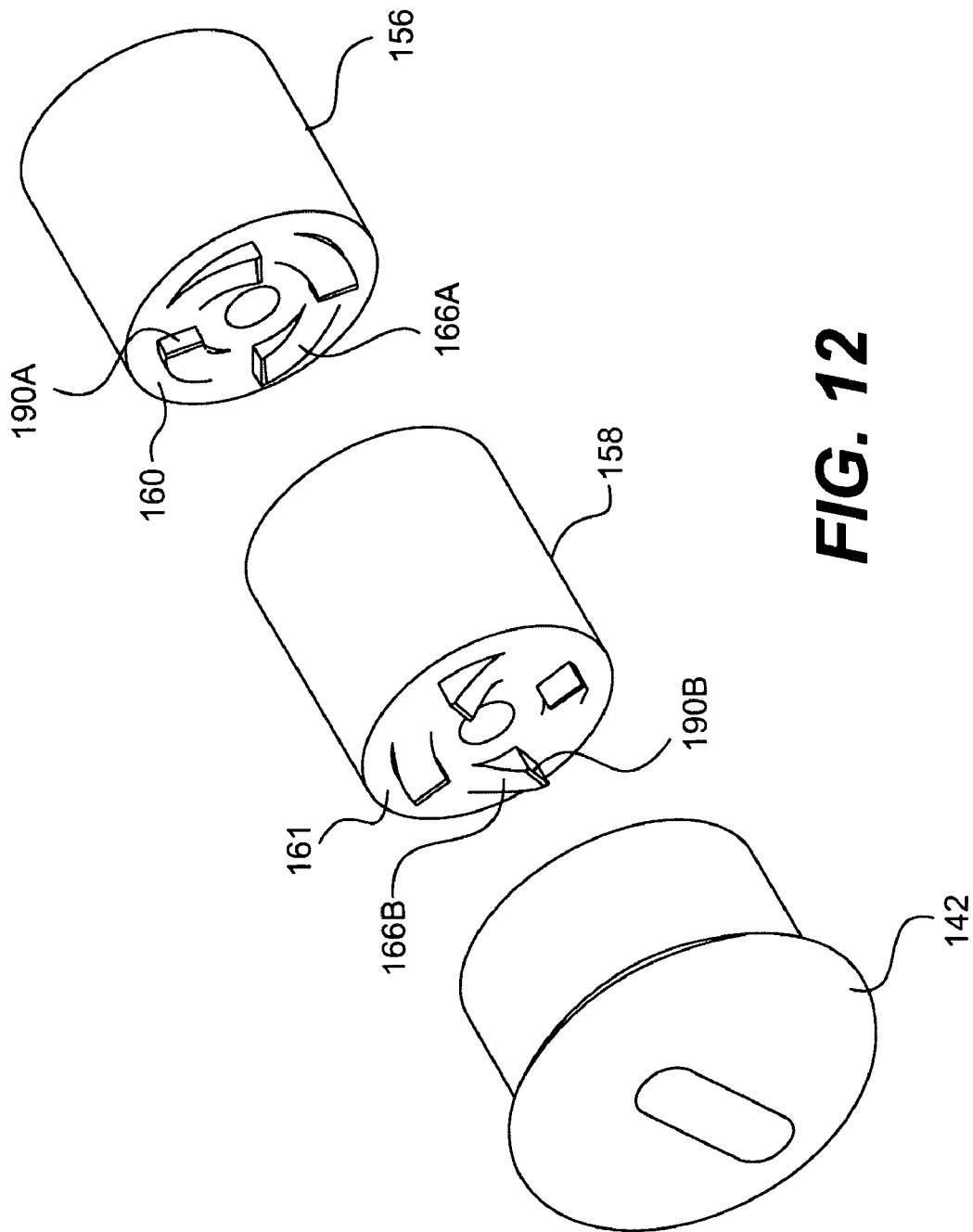
FIG. 12 is an enlarged isometric view showing the distal cap, the first camming element, and the second camming element shown in the previous figure.

FIG. 12 is an enlarged isometric view showing distal cap 142, first camming element 156, and second camming element 158 shown in the previous figure. With reference to FIG. 12, it will be appreciated that second camming element 158 comprises a plurality of ramped surfaces 166B and a plurality of faces 190B. Each ramped surface 166B is adjacent to a corresponding face 190B. In the embodiment of FIG. 12, each face 190B is generally perpendicular to a distal surface 161 of second camming element 158. In the embodiment of FIG. 12, distal cap 142 comprises a plurality of recesses that are dimensioned to receive ramped surfaces 166B. With reference to FIG. 12, it will be appreciated that first camming element 156 comprises a plurality of ramped surfaces 166A and a plurality of faces 190A. Each ramped surface 166A is adjacent to a corresponding face 190A. In the embodiment of FIG. 12, each face 190A is generally perpendicular to a distal surface 160 of first camming element 156. Second camming element 158 comprises a plurality of recesses that are dimensioned to receive ramped surfaces 166A in the embodiment of FIG. 12.

Figure 13:
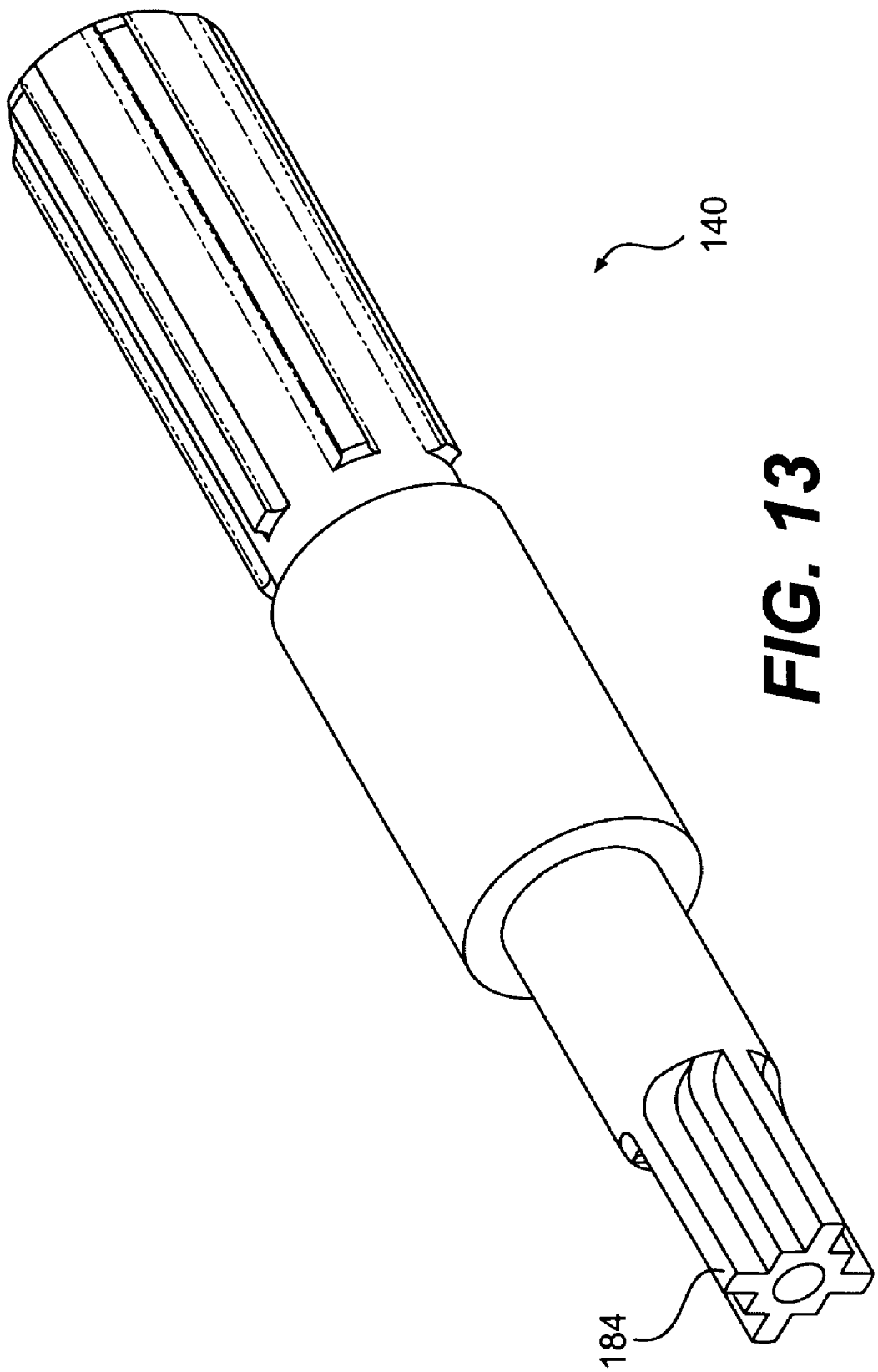
FIG. 13 is an isometric view of the handle axle.

FIG. 13 is an isometric view of handle axle 140. With reference to FIG. 13, it will be appreciated that a distal portion of handle axle 140 includes the plurality of splines 184.

Figure 14:
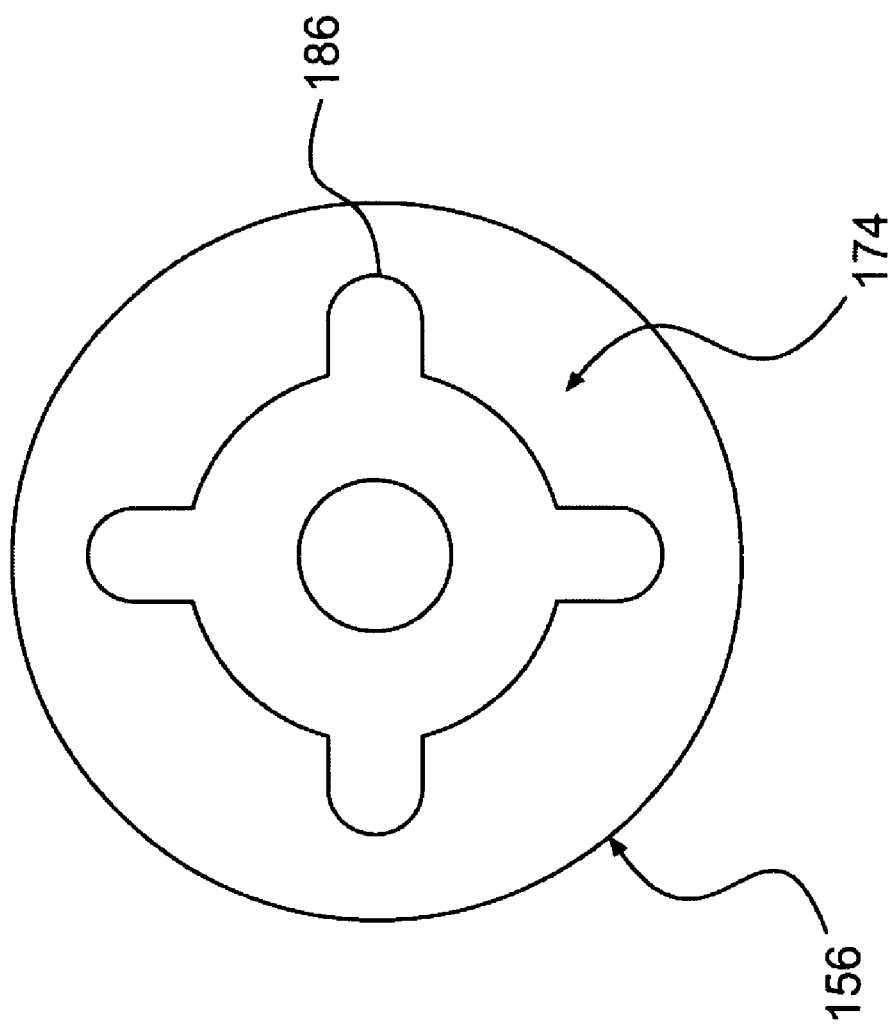
FIG. 14 is a plan view showing a proximal surface of the first camming element.

FIG. 14 is a plan view showing a proximal surface of first camming element 156. With reference to FIG. 14, it will be appreciated that first camming element 156 defines socket 174. In the embodiment of FIG. 14, socket 174 is dimensioned to received the distal portion of handle axle 140. With reference to FIG. 14, it will be appreciated that socket 174 includes grooves 186 that are dimensioned to receive the splines of handle axle 140 shown in the previous figure.

Figure 15:
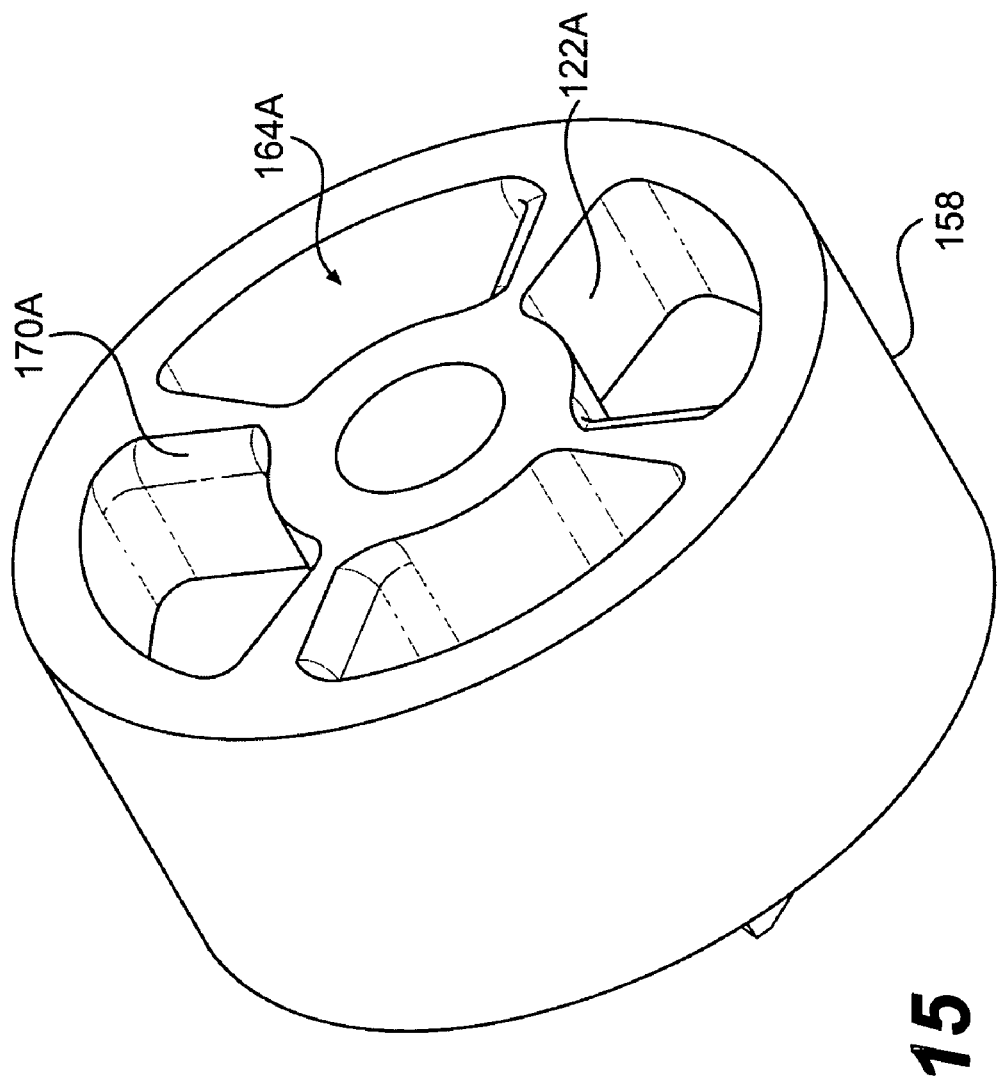
FIG. 15 is an enlarged isometric view showing a second camming element. The second camming element defines a plurality of recesses. Each recess is dimensioned to receive a ramped surface of the first camming element shown in the previous figure.

FIG. 15 is an enlarged isometric view showing second camming element 158. Second camming element 158 defines a plurality of recesses 164A. Each recess 164A is dimensioned to receive a ramped surface of first camming element 156 shown in the previous figure. Each recess 164A is partially defined by wall 122A. Each wall 122A includes a ramp engaging surface 170A. In the embodiment of FIG. 15, each ramp engaging surface 170A has a radius.

FIG. 16 is an enlarged isometric view showing distal cap 142. Distal cap 142 defines a plurality of recesses 164B. Each recess 164B is dimensioned to receive a ramped surface 166B of second camming element 158 shown in the previous figure. Each recess 164B is partially defined by a wall 122B. Each wall 122B includes a ramp engaging surface 170B. In the embodiment of FIG. 16, each ramp engaging surface 170B has a radius.

The operation of handle assembly 134 will now be described. A physician may fix handle assembly 134 about the proximal portion of shaft 136 of crossing device 132. Alternatively, crossing device 132 may be delivered to the physician with handle assembly 134 positioned on shaft 136.

During a therapy procedure, the physician may periodically adjust the position of handle assembly 134 along the length of shaft 136. To move the position of handle assembly 134 along shaft 136, the physician may loosen proximal cap 144 from handle axle 140 such that the tapered surfaces of the jaws of collet 146 are not in contact with the tapered surface of cavity 148 of handle axle 140. The physician may slide handle assembly 134 in a lengthwise direction along shaft 136 to a desired location. The physician may then tighten proximal cap 144 within handle axle 140. In this manner, the tapered surfaces of the jaws of collet 146 may contact the tapered surface of cavity 148 and cause the jaws of collet 146 to pinch shaft 136 and fix the position of shaft 136 relative to handle assembly 134.

During a therapy procedure, the physician may position the distal portion of shaft 136 of crossing device 132 within artery 102. Handle assembly 134 may be used to advance the distal portion of crossing device 132 to a location proximal of occlusion 101. Alternatively, or additionally, handle assembly 134 may be used to advance the distal portion of crossing device 132 between occlusion 101 and adventitia 124 to a location distal occlusion 101. In this manner, a physician may grip handle assembly 134 via handle housing 138 with the thumb and forefinger of one hand, or alternatively, with two hands. As shaft 136 is advanced into the vasculature of the patient, the physician may periodically adjust the position of handle assembly 134 along the length of shaft 136 as described above.

At various times during a therapy procedure, the physician may rotate handle housing 138 to rotate crossing device 132, including shaft 136 and tip 176. Rotating crossing device 132 assures that the coefficient of friction at the interface between the crossing device and the surrounding tissue will be a kinetic coefficient of friction and not a static coefficient of friction. In this manner, crossing device 132 may more easily pass through artery 102, occlusion 101, and/or various layers of the wall of artery 102. The physician may rotate handle housing 138 in a clockwise (CW) or in a counter-clockwise (CCW) direction.

For purposes of this disclosure, the clockwise and counter-clockwise are oriented from the perspective of a physician having the left hand (LH) and right hand (RH) shown in FIG. 4. This physician holding handle assembly 134 in his left hand (LH) and right hand (RH) is contemplating the rotation of the tip 176. In FIG. 4, the fingers of each hand are shown wrapping in a clockwise direction around shaft 136. In other words, clockwise and counter clockwise are viewed from the perspective of a viewer positioned near the proximal end of the device viewing an imaginary clock near the distal end of the device.

The physician causes shaft 136 and tip 176 to rotate by rotating handle housing 138. During this rotation, shaft 136 and tip 176 may experience resistance to rotation. This resistance may, for example, be caused by frictional contact between crossing device 132 and features of the patient's anatomy (e.g., the walls of a blood vessel and occlusions located inside the blood vessel). When resistance is encountered, the physician may apply greater torque to shaft 136, up to a predetermined maximum torque. In the exemplary embodiment of FIGS. 3 through 14, this predetermined maximum torque is controlled by a torque control mechanism 154.

The operation of torque control mechanism 154 may be described with reference to the exemplary embodiment shown in FIGS. 3 through 14. In this exemplary embodiment, distal cap 142 is fixed to handle housing 138 by a threaded connection. Accordingly, rotation of handle housing 138 in a CCW direction causes distal cap 142 to also rotate in a CCW direction. Wall 122B of distal cap 142 may then contact face 190B of ramp 166B, causing second camming element 158 to rotate in a CCW direction. The rotation of second camming element 158 may rotate ramp engaging surface 170A of second camming element 158 into contact with ramp 166A of first camming element 156. Specifically, ramp engaging surface 170A may contact, or "ride," a lower portion of the length of ramp 166A. The contact between ramp engaging surface 170A and ramp 166A causes first camming element 156 to rotate in the CCW direction. Because handle axle 140 is fixed to first camming element 156 by the plurality of splines 184, rotation of first camming element 156 causes handle axle 140 to rotate in the CCW direction. As described above, shaft 136 is fixed to handle axle 140 by collet 146. Accordingly, rotation of handle axle 140 in the CCW direction causes shaft 136 to rotate in the CCW direction.

As handle housing 138 continues to rotate in the CCW direction, the resistance to rotation that shaft 136 and tip 176 experience may increase. As this resistance increases, the torque required to rotate shaft 136 may increase. As the torque applied to handle housing 138 increases, ramp engaging surface 170A may ride further up the length of ramp 166A (i.e. from a lower portion to a higher portion). When this is the case, ramp engaging surface 170A of second camming element 158 and ramp 166A of first camming element 156 will cooperate to compress spring 168.

In the exemplary embodiment shown in FIGS. 3 through 14, torque control mechanism 154 limits the magnitude of torques that may be applied to shaft 136 by rotating handle housing 138. Torque control mechanism 154 limits the torque in a first direction to a magnitude equal to or less than a first maximum torque and limits the torque in a second direction to a magnitude equal to or less than a second maximum torque. In some useful embodiments, the second maximum torque is different from the first maximum torque. In these embodiments, the shape (e.g., the height) of each ramp 166B of second camming element 158 may be different from the shape of each ramp 166A of first camming element 156.

When the first maximum torque is applied to shaft 136, sufficient force is exerted against spring 168 to allow ramp engaging surface 170A to ride up the entire length of ramp 166A and over the highest point of ramp 166A. When ramp engaging surface 170A rides over the highest point of ramp 166A, spring 168 causes proximal end 162 of second camming element 158 to rapidly contact distal end 160 of first camming element 156. This rapid contact may generate an audible "clicking" sound. This rapid contact may also cause a tactile response (e.g., vibrations in housing handle 138) that can be felt in the finger tips of left hand (LH) and right hand (RH). This audible and/or tactile response may serve to notify the physician that the first maximum torque has been exceeded.

When the first maximum torque has been reached, continued rotation of handle housing 138 in the CCW direction will cause no further substantial rotation of shaft 136. Instead, continued rotation of handle housing 138 will only produce more "clicking" by torque control mechanism 154. Between a minimum amount of torque necessary to rotate shaft 136 and the first maximum torque may represent a range of torque that may be applied to shaft 136 to cause rotation of shaft 136 in the CCW direction.

When the first maximum torque has been reached, the physician may choose to discontinue rotating handle housing 138 in the CCW direction. At this point, the physician may choose to begin rotating handle housing 138 in the CW direction. In some applications, reversing the direction of rotation is a useful strategy for crossing restrictions.

As mentioned above, torque control mechanism 154 also limits the magnitude of torque that may be applied to shaft 136 when handle housing 138 is rotated in a clockwise (CW) direction. The operation of torque control mechanism 154 when handle housing 138 is rotated in the CW direction may be described with continuing reference to the exemplary embodiment shown in FIGS. 3 through 14. In this exemplary embodiment, distal cap 142 is fixed to handle housing 138 by a threaded connection. Accordingly, rotation of handle housing 138 in the CW direction causes distal cap 142 to also rotate in the CW direction. Rotation of distal cap 142 in the CW direction will rotate ramp engaging surface 170B of distal cap 142 into contact with ramp 166B of second camming element 158. Specifically, the radius of ramp engaging surface 170B may contact, or "ride," a lower portion of the length of ramp 166B. This contact causes second camming element 158 to rotate in the CW direction. Rotating second camming element 158 in the CW direction causes a wall 122A of second camming element 156 to contact a face 190A of first camming element 156, causing first camming element 156 to rotate in the CW direction. Because handle axle 140 is fixed to first camming element 156 by the plurality of splines 184, rotation of first camming element 156 causes handle axle 140 to rotate. As describe above, shaft 136 is fixed to handle axle 140 by collet 146. Therefore, shaft 136 rotates in the CW direction when handle axle 140 is rotated in the CW direction.

As handle housing 138 continues to rotate in the CW direction, the resistance to rotation that shaft 136 experiences may increase. As this resistance increases, the torque required to overcome the resistance may increase and may result in a higher torque being applied to shaft 136. As the torque increases, ramp engaging surface 170B will ride further up the length of ramp 166B (i.e. from a lower portion to a higher portion). When this is the case, ramp engaging surface 170B and ramp 166B of second camming element 158 will cooperate to compress spring 168.

When the second maximum torque is applied to shaft 136, sufficient force is exerted against spring 168 to allow ramp engaging surface 170B to ride up the entire length of ramp 166B and over the highest point of ramp 166B. At this point, continued rotation of handle housing 138 in the CW direction will result in substantially no further rotation of shaft 136. Instead, continued rotation of handle housing 138 will only produce more "clicking" by torque control mechanism 154.

The "clicking" by torque control mechanism 154 is produced, for example, as second camming element 158 rapidly contacts distal cap 142. When ramp engaging surface 170B rides over the highest point of ramp 166B, spring 168 causes distal end 161 of second camming element 158 to rapidly contact proximal end 163 of distal cap 142. In some exemplary embodiments, this rapid contact generates an audible "clicking" sound. This rapid contact may also cause a tactile response (e.g., vibrations in housing handle 138) that can be felt in the finger tips of left hand (LH) and right hand (RH). This audible and/or tactile response may serve to notify the physician that the second maximum torque has been exceeded. Between a minimum amount of torque necessary to rotate shaft 136 and the second maximum torque may represent a range of torque that may be applied to shaft 136 to cause rotation of shaft 136 in the CW direction.

The first maximum torque and the second maximum torque may be varied by varying a number of attributes of torque control mechanism 154. Examples of attributes include the spring constant of spring 168, a magnitude of pre-loading placed on spring 168, the maximum height of each ramp (166A, 166B), and the slope/pitch/angle of each ramp (166A, 166B). The first and second maximum torques may be simultaneously increased or decreased by replacing spring 168 with a spring producing greater or lesser spring force. The first and second maximum torques may be independently changed by altering the dimensions of one or more of the components of torque control mechanism 154, such as, for example, the maximum height of each ramp (166A, 166B), the slope/pitch/angle of each ramp (166A, 166B), characteristics of ramp engaging surface 170A and/or ramp engaging surface 170B, or any other modification that would result in a greater or lesser first and/or second maximum torques.

The desired first maximum torque and the desired second maximum torque may be related to the strength of shaft 136 relative to the rotational direction. By way of example, when shaft 136 is rotated in a CCW direction, coil 172 of shaft 136 may expand and may be weaker. In this case, the first maximum torque, i.e. the maximum torque applied in the CCW direction should be low enough to not break the expanded coil 172. In a further example, when shaft 136 is rotated in a CW direction, coil 172 of shaft 136 may compress and may be stronger relative to the steady or expanded state of coil 172. In this case, the second maximum torque, i.e. the maximum torque applied in the CW direction should be low enough to not break the compressed coil 172. In this example, the second maximum torque would be higher than the first maximum torque. It is further contemplated that the first and second maximum torques may not be the exact torque necessary to cause coil 172 to fail in a respective direction, but that there may be safety factor included in determining the torques.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for facilitating treatment of a blood vessel, the device comprising:
a shaft having a distal end and a proximal end;
a handle assembly fixed about the proximal end of the shaft, the handle assembly including a first portion, wherein rotation of the first portion in a first direction about a longitudinal axis of the shaft causes rotation of the shaft in the first direction when a torque applied by the first portion to the shaft is below a first maximum torque;
a first camming element having a protrusion that includes a first ramped surface and a second surface; and
a second camming element having a wall,
wherein rotation of the first portion in the first direction about the longitudinal axis of the shaft does not cause rotation of the shaft in the first direction when the torque applied by the first portion to the shaft is above the first maximum torque, wherein the first ramped surface is configured to allow the wall of the second camming element to pass over a top of the protrusion when the first camming element is rotated with respect to the second camming element in the first direction, and the second surface is configured to prevent the wall of the second camming element from passing over a top of the protrusion when the first camming element is rotated with respect to the second camming element in a second direction,
wherein the shaft is an elongate shaft comprising one or more flexible elements, the shaft being configured to traverse along a blood vessel.

2. The device of claim 1, wherein the handle assembly provides an audible indication when the torque applied by the first portion to the shaft is above the first maximum torque.

3. The device of claim 2, wherein the audible indication comprises a clicking sound.

4. The device of claim 1, wherein the handle assembly provides a tactile indication when the torque applied by the first portion to the shaft is above the first maximum torque.

5. The device of claim 4, wherein the tactile indication comprises vibration of the first portion of the handle assembly.

6. The device of claim 1, wherein rotation of the first portion in a second direction about the longitudinal axis of the shaft causes rotation of the shaft in the second direction when a torque applied by the first portion to the shaft is below a second maximum torque.

7. The device of claim 6, wherein rotation of the first portion in the second direction about the longitudinal axis of the shaft does not cause rotation of the shaft in the second direction when the torque applied by the first portion to the shaft is above the second maximum torque.

8. The device of claim 6, wherein the second maximum torque is greater than the first maximum torque.

9. The device of claim 6, wherein the handle assembly provides an audible indication when the torque applied by the first portion to the shaft is above the second maximum torque.

10. The device of claim 9, wherein the audible indication comprises a clicking sound.

11. The device of claim 6, wherein the handle assembly provides a tactile indication when the torque applied by the first portion to the shaft is above the second maximum torque.

12. The device of claim 11, wherein the tactile indication comprises vibration of the first portion of the handle assembly.

13. The device of claim 1, further including a torque limiting mechanism, the torque limiting mechanism including a set of camming elements.

14. The method of claim 13, wherein the set of camming elements includes the first camming element, the second camming element disposed between the first camming element and a third camming element, wherein the third camming element is fixed to the first portion.

15. The device of claim 14, wherein the second camming element is rotatable about the longitudinal axis relative to the first camming element and the third camming element.

16. The device on claim 14, wherein the second camming element defines at least one recess configured to receive the protrusion of the first camming element.

17. The device of claim 14, wherein the handle assembly further includes:
a second portion including a handle axle; and
a cap threadedly engaged to the handle axle.

18. The device of claim 17, wherein a portion of the handle axle is disposed within the first camming element.

19. The device of claim 17, wherein the second portion of the handle assembly further includes a collet configured to secure the shaft to the second portion of the handle assembly.

20. The device of claim 17, wherein the first camming element defines an opening configured to receive a portion of the handle axle.

21. The device of claim 20, wherein the handle axle includes a plurality of splines, and wherein a portion of the plurality of splines is disposed within the first camming element.

22. The device of claim 14, wherein the first portion of the handle assembly includes a handle housing threadedly engaged to the third camming element.

23. The device of claim 22, wherein the third camming element is a cap.

24. The device of claim 14, wherein the second camming element defines at least one ramped surface.

25. The device on claim 24, wherein the third camming element defines at least one recess configured to receive the at least one ramped surface of the second camming element.

26. The device of claim 1, wherein the second surface of the protrusion of the first camming element is substantially parallel to the longitudinal axis.

27. The device of claim 1, wherein the second camming element is located distally of the first camming element.

28. The device of claim 1, wherein the first ramped surface is configured to allow the wall of the second camming element to pass over the top of the protrusion only when the torque applied by the first portion to the shaft is above the first maximum torque.

29. A medical device including:
   a shaft; and
   a handle assembly, the handle assembly including:
      a first portion, wherein rotation of the first portion in a first direction about a longitudinal axis of the shaft causes rotation of the shaft in the first direction when a torque applied by the first portion to the shaft is below a first maximum torque;
      a torque limiting mechanism in communication with the first portion, the torque limiting mechanism including:
         a first camming element having a protrusion that includes a first ramped surface and a second surface; and
         a second camming element having a wall,
      wherein rotation of the first portion in the first direction about the longitudinal axis of the shaft does not cause rotation of the shaft in the first direction when the torque applied by the first portion to the shaft is equal to or above the first maximum torque, wherein the first ramped surface is configured to allow the wall of the second camming element to pass over a top of the protrusion when the first camming element is rotated with respect to the second camming element in the first direction, and the second surface is configured to prevent the wall of the second camming element from passing over a top of the protrusion when the first camming element is rotated with respect to the second camming element in a second direction,
      wherein the shaft is an elongate shaft comprising one or more flexible elements, the shaft being configured to traverse along a blood vessel.

30. The device of claim 29, wherein rotation of the first portion in a second direction about the longitudinal axis of the shaft causes rotation of the shaft in the second direction when a torque applied by the first portion to the shaft is below a second maximum torque.

31. The device of claim 30, wherein rotation of the first portion in the second direction about the longitudinal axis of the shaft does not cause rotation of the shaft in the second direction when the torque applied by the first portion to the shaft is above the second maximum torque.

32. The device of claim 30, wherein the second maximum torque is different than the first maximum torque.

33. The device of claim 32, wherein the first portion of the handle assembly includes a handle housing threadedly engaged to the third camming element.

34. The device of claim 29, wherein the torque limiting mechanism further includes a third camming element.

35. The device of claim 34, wherein the second camming element is disposed between the first camming element and the third camming element, and the third camming element is fixed to the first portion.

36. The device of claim 35, wherein the second camming element is rotatable about the longitudinal axis relative to the first camming element and the third camming element.

37. The device of claim 35, wherein the handle assembly further includes:
   a second portion including a handle axle; and
   a cap threadedly engaged to the handle axle.

38. The device of claim 29, wherein the second surface of the protrusion of the first camming element is substantially parallel to the longitudinal axis.

39. The device of claim 29, wherein the second camming element is located distally of the first camming element.

40. The device of claim 29, wherein the first ramped surface is configured to allow the wall of the second camming element to pass over the top of the protrusion only when the torque applied by the first portion to the shaft is above the first maximum torque.

41. A device for facilitating treatment of a blood vessel, the device comprising:
   a shaft having a distal end and a proximal end;
   a handle assembly disposed about the shaft;
   a first camming element having a protrusion that includes a first ramped surface and a second surface; and
   a second camming element having a wall,
   the handle assembly comprising a first portion and a torque limiting mechanism coupling the first portion to the shaft;
   wherein the torque limiting mechanism allows relative movement between the first portion and the shaft when the first portion is being rotated in a first direction and a torque applied to the shaft has exceeded a first maximum torque, wherein the first ramped surface is configured to allow the wall of the second camming element to pass over a top of the protrusion when the first camming element is rotated with respect to the second camming element in the first direction, and the second surface is configured to prevent the wall of the second camming element from passing over a top of the protrusion when the first camming element is rotated with respect to the second camming element in a second direction,
   wherein the shaft is an elongate shaft comprising one or more flexible elements, the shaft being configured to traverse along a blood vessel.

42. The device of claim 41, wherein the torque limiting mechanism allows relative movement between the first portion and the shaft when the first portion is being rotated in a second direction and the torque applied to the shaft has exceeded a second maximum torque.

43. The device of claim 42, wherein the second maximum torque is different than the first maximum torque.

44. The device of claim 42, wherein:
   the shaft comprises a left hand wound coil;
   the first direction is a clockwise direction; and
   the first maximum torque is greater than the second maximum torque.

45. The device of claim 42, wherein:
   the shaft comprises a right hand wound coil;
   the second direction is a counterclockwise direction; and
   the second maximum torque is greater than the first maximum torque.

46. The device of claim 41, wherein the shaft comprises a coil.

47. The device of claim 46, further comprising a distal tip fixed to a distal end of the coil and a proximal hub fixed to a proximal end of the coil.

48. The device of claim 41, wherein the torque limiting mechanism transfers torque between the first portion and the shaft when the first portion is being rotated in a first direction and the torque applied to the shaft is less than or equal to the first maximum torque.

49. The device of claim 41, wherein the torque limiting mechanism includes the first camming element.

50. The device of claim 49, wherein the first camming element is coupled to the shaft so that the first camming element is not free to rotate relative to the shaft.

51. The device of claim 49, wherein the torque limiting mechanism includes the second camming element.

52. The device of claim 51, wherein the second camming element includes:
  a protrusion including a first ramped surface and a second surface; and
  a first ramp engaging surface.

53. The device of claim 52, wherein the torque limiting mechanism comprises a cap fixed to the first portion, the cap having a wall configured to interact with the second surface of the second camming element and a second ramp engaging surface configured to interact with the first ramped surface of the second camming element.

54. The device of claim 53, wherein:
  the first ramp engaging surface of the second camming element engages the first ramped surface of the first camming element when the first portion is rotated in the first direction; and
  the second ramp engaging surface of the cap engages the first ramped surface of the second camming element when the first portion is rotated in a second direction.

55. The device of claim 53, wherein:
  the protrusion of the first camming element has a first shape;
  the protrusion of the second camming element has a second shape; and
  the second shape is different than the first shape.

56. The device of claim 53, wherein:
  the first ramped surface of the first camming element has a first pitch;
  the first ramped surface of the second camming element has a second pitch; and
  the second pitch is different from the first pitch.

57. The device of claim 53, wherein:
  the protrusion of the first camming element has a first maximum height;
  the protrusion of the second camming element has a second maximum height; and
  the second maximum height is different than the first maximum height.

58. The device of claim 53, wherein the first ramp engaging surface travels over and beyond the first ramped surface of the first camming element when the first portion is being rotated in the first direction and the torque applied to the shaft has exceeded the first maximum torque, and wherein the second ramp engaging surface travels over and beyond the first ramped surface of the second camming element when the first portion is being rotated in a second direction and a torque applied to the shaft has exceeded a second maximum torque.

59. The device of claim 41, wherein the second surface of the protrusion of the first camming element is substantially parallel to a longitudinal axis of the device.

60. The device of claim 41, wherein the second camming element is located distally of the first camming element.

61. The device of claim 41, wherein the first ramped surface is configured to allow the wall of the second camming element to pass over the top of the protrusion only when the torque applied by the first portion to the shaft is above the first maximum torque.

* * * * *